(12) United States Patent
Coleman

(10) Patent No.: US 10,123,855 B1
(45) Date of Patent: Nov. 13, 2018

(54) ORTHODONTIC DEVICES FOR MOVEMENT OF IMPACTED OR MALPOSITIONED TEETH

(71) Applicant: Grant G. Coleman, Charlotte, NC (US)

(72) Inventor: Grant G. Coleman, Charlotte, NC (US)

(*) Notice: Subject to any disclaimer, the term of this patent is extended or adjusted under 35 U.S.C. 154(b) by 630 days.

(21) Appl. No.: 14/537,838

(22) Filed: Nov. 10, 2014

Related U.S. Application Data

(60) Provisional application No. 61/901,542, filed on Nov. 8, 2013.

(51) Int. Cl.
A61C 3/00 (2006.01)
A61C 7/36 (2006.01)
A61C 7/16 (2006.01)

(52) U.S. Cl.
CPC . *A61C 7/36* (2013.01); *A61C 7/16* (2013.01)

(58) Field of Classification Search
CPC ..................................... A61C 7/36; A61C 7/31
USPC ....................................................... 433/18, 21
See application file for complete search history.

(56) References Cited

U.S. PATENT DOCUMENTS

| | | | |
|---|---|---|---|
| 3,127,677 A | 4/1964 | Schachter | |
| 3,508,332 A * | 4/1970 | Armstrong | A61C 7/12 433/21 |
| 3,835,538 A | 9/1974 | Northcutt | |
| 4,187,610 A | 2/1980 | Ziegler | |
| 4,256,456 A | 3/1981 | Wallshein | |
| 4,869,667 A | 9/1989 | Vardimon | |
| 5,035,614 A * | 7/1991 | Greenfield | A61C 7/12 433/18 |
| 5,112,221 A | 5/1992 | Terry | |
| 5,246,366 A | 9/1993 | Tracey | |
| 5,312,247 A | 5/1994 | Sachdeva et al. | |
| 5,545,037 A * | 8/1996 | Takeshi | A61C 7/36 433/19 |
| 5,697,782 A * | 12/1997 | Klapper | A61C 7/36 433/19 |
| 5,846,074 A * | 12/1998 | Klapper | A61C 7/36 433/19 |
| 6,217,324 B1 * | 4/2001 | Kesling | A61C 7/00 433/14 |
| 6,273,713 B1 * | 8/2001 | Liou | A61C 7/36 433/19 |
| 7,335,021 B2 | 2/2008 | Nikodem | |
| 2003/0068595 A1 | 4/2003 | Pitnick et al. | |
| 2005/0064359 A1 * | 3/2005 | Nikodem | A61C 7/00 433/18 |
| 2006/0068354 A1 * | 3/2006 | Jeckel | A61C 7/00 433/21 |

(Continued)

*Primary Examiner* — Nicholas Lucchesi
(74) *Attorney, Agent, or Firm* — Tillman Wright, PLLC; James D. Wright; David R. Higgins

(57) ABSTRACT

A method of using an orthodontic device to effect movement of an impacted or malpositioned tooth includes providing an orthodontic device, the orthodontic device including a bracket, a coiled spring, and an anchoring assembly, bonding the bracket to an impacted or malpositioned tooth, connecting a first end of the spring to a first spring attachment portion supported by the bracket, connecting a second end of the spring to a second spring attachment portion supported by the anchoring assembly, and coupling the anchoring assembly to a second orthodontic device that is installed in the patient's mouth.

19 Claims, 38 Drawing Sheets

(56) References Cited

U.S. PATENT DOCUMENTS

| | | | |
|---|---|---|---|
| 2007/0196781 A1* | 8/2007 | Cope | A61C 7/00 433/18 |
| 2008/0138759 A1* | 6/2008 | Kravitz | A61C 7/00 433/21 |
| 2008/0182219 A1 | 7/2008 | Spalty | |
| 2009/0197216 A1* | 8/2009 | Miller | A61C 7/36 433/19 |
| 2010/0178628 A1* | 7/2010 | Kim | A61C 7/12 433/10 |
| 2010/0307511 A1* | 12/2010 | Meade | A61F 5/566 128/848 |
| 2011/0269094 A1* | 11/2011 | Shearer | A61C 7/36 433/19 |
| 2012/0058444 A1* | 3/2012 | Allesee | A61C 7/22 433/21 |
| 2012/0202162 A1 | 8/2012 | Hilgers et al. | |
| 2013/0149659 A1 | 6/2013 | Garnett | |
| 2014/0242536 A1* | 8/2014 | Ziehmer | A61C 7/36 433/19 |
| 2015/0257858 A1* | 9/2015 | Dischinger | A61C 7/36 433/19 |

* cited by examiner

20

20

ORTHODONTIC DEVICES FOR MOVEMENT OF IMPACTED OR MALPOSITIONED TEETH

CROSS-REFERENCE TO RELATED APPLICATION

The present application is a U.S. nonprovisional patent application of, and claims priority under 35 U.S.C. § 119(e) to, U.S. provisional patent application Ser. No. 61/901,542, filed Nov. 8, 2013 and entitled "ORTHODONTIC DEVICES FOR MOVEMENT OF IMPACTED OR MALPOSITIONED TEETH," which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to orthodontic devices, and, in particular, to orthodontic devices for movement of impacted or malpositioned teeth.

Background

Orthodontics is the science of moving teeth within the mouth by the application of force to the teeth over time. Generally, the goal of orthodontic treatment is to ideally align the upper and lower teeth within their respective arches and jaws so that the teeth are both esthetically pleasing in appearance, and so that they also fit in the anatomically prescribed ideal positions. Frequently during orthodontic treatment, one or more teeth may fail to erupt or may erupt into a significantly non-ideal position. In such cases, the application of orthodontic force to such a tooth is required to move it closer to its ideal position within its respective dental arch.

Previous methods of moving such malpositioned or impacted teeth involved a surgical procedure to expose at least part of the involved tooth, followed by the bonding of some sort of chain-like attachment to the tooth as an attachment for an orthodontic force. Frequently, the orthodontic force would be applied via some sort of elastomeric thread or similar device tied to the chain, which would provide a very high level of force immediately upon insertion and activation. Unfortunately, this high level of force decreases rapidly, over only a few days, as the involved tooth began to move, requiring frequent reactivation by the orthodontist in order to keep pressure on the tooth for it to continue its movement.

This presents a problem in that the patient must return to the orthodontist very frequently for additional adjustments. Furthermore, multiple orthodontic studies have confirmed that teeth move best when the applied orthodontic force is both light and constant, or at least relatively constant. The aforementioned method of orthodontically moving an impacted tooth provided heavy, inconsistent (or "intermittent") force to teeth, which has been shown to increase patient discomfort, result in slower tooth movement, and increase the risk of damage to the involved tooth. Thus, in order to provide a more efficient, less-painful, and safer method of moving an impacted or partially-impacted tooth, a need exists for a device designed to allow application of a lighter, continuous force to the tooth over time with less need for activation by the orthodontist.

Previous devices have been described in which the active portion of the device that is applying the orthodontic force consists of a "substantially planar device" made of some sort of superelastic metal. "Substantially planar" suggests that this portion of the appliance essentially lies within one plane of space or is "flat" in the essence of its form. This presents several problems, however, when it comes to applying ideal orthodontic forces within the oral cavity. Because of the requirement that the load-applying portion of the previously-described devices be "substantially planar," the amount of superelastic wire that can be incorporated into the appliance is limited. This, in turn, results in several shortcomings when it comes to orthodontic tooth movement of an impacted or partially-impacted tooth.

First, a substantially planar design impacts the load-deflection rate (LDR) of the spring. The LDR pertains to the force, or load, that an orthodontic appliance, usually a wire, exerts when it is deformed from its original position. In most cases, the load increases the more that an appliance is activated (the load does taper and "plateau" for super elastic wires at some point). One way to reduce the LDR and keep it within a desired range is to incorporate a very large amount of wire into a small space, i.e. through loops or coils. A coil spring by nature is a design that incorporates an enormous amount of wire into a relatively short linear distance. Coil springs, therefore, can be stretched or activated over a large distance while still maintaining a relatively low LDR, keeping the force in a biologically-friendly range. Unfortunately, "substantially planar devices" potentially have a higher LDR over a shorter range of activation than a coil spring.

A substantially planar design also may suffer from permanent deformation, which is what can occur if a wire is stretched beyond its Elastic Limit, the point at which it can no longer return to its original shape without distortion. One way to avoid permanent deformation of a wire is to incorporate as much wire as possible into a given length, i.e. by coiling or looping the wire. Coil springs, therefore, are commonly used to provide orthodontic force because they can be activated over a large distance without undergoing permanent deformation, thus keeping the spring fully active. Permanent deformation of a wire or spring can reduce the load applied by the device or even render it inactive in an extreme case. So, using a coil spring that incorporates a large length of wire into a relatively short distance reduces the risk that the appliance will undergo permanent deformation when activated over a given distance. Unfortunately, a substantially planar device potentially has a greater chance of permanent deformation than does a coil spring because it incorporates less length of wire over the same linear distance.

Still further, it may be necessary for a substantially planar design to have a larger size in order to maintain functionality. In particular, in order to incorporate a large amount of wire into a "substantially planar" device, the active wire portion of the device must be made wider within that plane of space. Unfortunately, because the device is to be used intraorally, and in some cases will be actually covered with gingival tissue following the surgical exposure of the tooth and attachment of the device to the impacted or partially impacted tooth, its size is extremely important, and making the device substantially wider in order to incorporate more wire into its design could cause it to be more bulky and therefore potentially damaging to the oral tissues which cover it. Furthermore, excessive width of the active portion of the device could also make it more difficult for the orthodontist or surgeon to place it in the mouth without interference from adjacent teeth or tissues. This is potentially inferior to a coil spring, which by design incorporates a large amount of wire into a relatively small space from both a width and length standpoint.

A need exists for a device that is much smaller than previously described "substantially planar" devices, making it much less bulky, more tissue friendly, and easier to place, and which, when "activated" or stretched, has a design and size that causes less damage to overlying tissue than might a wider "substantially planar" device.

SUMMARY OF THE PRESENT INVENTION

Broadly defined, the present invention according to one aspect is an orthodontic device for movement of an impacted or malpositioned tooth, as shown and described.

Broadly defined, the present invention according to another aspect is a method of using an orthodontic device for movement of an impacted or malpositioned tooth, as shown and described.

Broadly defined, the present invention according to another aspect is an orthodontic device for movement of an impacted or malpositioned tooth, including: a bondable bracket; a spring connected at one end to the bracket; and an anchoring assembly connected to an opposite end of the spring.

In a feature of this aspect, the bondable bracket includes a bondable metal pad or button and a spring attachment portion to which the spring is connected. In a further feature, the spring attachment portion includes at least one slot through which the spring is routed.

In another feature of this aspect, the spring is a coil spring.

In another feature of this aspect, the anchoring assembly includes an anchoring feature and a spring attachment portion. In further features, the spring attachment portion includes at least one slot through which the spring is routed; and/or the anchoring feature includes a hook. In a still further feature, the hook is adapted to be coupled to an archwire installed in a patient's mouth.

Broadly defined, the present invention according to another aspect is a method of using an orthodontic device for movement of an impacted or malpositioned tooth, including: providing a first orthodontic device, the first orthodontic device including a bracket, a spring, and an anchoring assembly; bonding the bracket to an impacted or malpositioned tooth; connecting one end of the spring to the bracket; connecting the anchoring assembly to an opposite end of the spring; and coupling the anchoring assembly to a second orthodontic device that is installed in the patient's mouth.

In a feature of this aspect, the method further includes a step, prior to the bonding step, of surgically opening gum tissue of a patient to reveal the impacted or malpositioned tooth.

In another feature of this aspect, the bondable bracket includes a bondable metal pad or button and a spring attachment portion to which the spring is connected. In a further feature, the spring attachment portion includes at least one slot through which the spring is routed.

In another feature of this aspect, the spring is a coil spring.

In another feature of this aspect, the anchoring assembly includes an anchoring feature and a spring attachment portion. In further features, the spring attachment portion includes at least one slot through which the spring is routed; and/or the anchoring feature includes a hook. In a still further feature, the step of coupling the anchoring assembly to an orthodontic device includes coupling the hook to an archwire.

Broadly defined, the present invention according to another aspect is an orthodontic device for effecting movement of an impacted or malpositioned tooth, including: a bracket including a button or pad that is bondable to an impacted or malpositioned tooth; an anchoring assembly including an anchoring feature or archwire bracket that may be coupled to an archwire and a spring attachment portion; and a spring secured at a first end to the bracket and secured at a second end to the spring attachment portion of the anchoring assembly.

In a feature of this aspect, the bracket further includes a spring attachment portion to which the coiled spring is secured at its first end. In further features, the spring attachment portion includes a rigid loop extending from the button or pad; the first end of the spring extends through the loop; the first end of the spring is welded to a main portion of the button or pad; the first end of the spring is welded to a main portion of the button or pad on both sides of the loop; a ball or other body is formed at the first end of the spring so as to prevent the spring from being withdrawn from the loop; the rigid loop is a first rigid loop, and wherein the spring attachment portion includes a second rigid loop through which the first end of the spring also extends; the spring attachment portion is connected to the button or pad via a standoff portion; the spring attachment portion is parallel to a main portion of the button or pad; the standoff portion extends perpendicularly from a main portion of the button or pad; the standoff portion extends perpendicularly from the spring attachment portion; the standoff portion includes a relief opening along at least one edge thereof to facilitate manufacture; the spring attachment portion is co-planar with, and extends away from, a main portion of the button or pad; the spring attachment portion includes at least one slot through which the spring is routed; the at least one slot includes a pair of separate slot openings; the at least one slot includes a pair of conjoined slot openings; the conjoined slot openings are partially separated by a peg; and/or the spring is threaded through the at least one slot.

In another feature of this aspect, the spring is a coil spring. In further features, the first end of the coil spring is threaded through at least one slot in a spring attachment portion of the bondable bracket; the first end of the coil spring is threaded through a pair of slots in the spring attachment portion of the bondable bracket; the coil spring defines a longitudinal axis, and wherein the longitudinal axis of the coil spring is co-planar with the spring attachment portion of the bondable bracket; the coil spring defines a longitudinal axis, and wherein the longitudinal axis of the coil spring is co-planar with a main portion of the button or pad; the second end of the coil spring is threaded through at least one slot in the spring attachment portion of the anchoring assembly; the first end of the coil spring is threaded through a pair of slots in the spring attachment portion of the anchoring assembly; the coil spring defines a longitudinal axis, and wherein the longitudinal axis of the coil spring is co-planar with the spring attachment portion of the anchoring assembly; and/or the coil spring defines a longitudinal axis, and wherein the longitudinal axis of the coil spring is co-planar with a main portion of the anchoring feature or archwire bracket.

In another feature of this aspect, the spring attachment portion is connected to the anchoring feature or archwire bracket via a standoff portion; the spring attachment portion is parallel to a main portion of the anchoring feature or archwire bracket; the standoff portion extends perpendicularly from a main portion of the anchoring feature or archwire bracket; the standoff portion extends perpendicularly from the spring attachment portion; the standoff portion includes a relief opening along at least one edge thereof to facilitate manufacture; and/or the spring attachment portion is co-planar with, and extends away from, a main portion of the anchoring feature or archwire bracket.

In another feature of this aspect, the spring attachment portion includes at least one slot through which the spring is routed; the at least one slot includes a pair of separate slot openings; the at least one slot includes a pair of conjoined slot openings; the conjoined slot openings are partially separated by a peg; and/or the spring is threaded through the at least one slot.

In another feature of this aspect, the anchoring feature or archwire bracket includes a hook; the hook is a round hook; the hook is a rectangular hook; the rectangular hook includes an angled tip; and/or the angled tip may be crimped around the archwire.

Broadly defined, the present invention according to another aspect is an orthodontic device for effecting movement of an impacted or malpositioned tooth, including: a bracket including a button or pad that is bondable to an impacted or malpositioned tooth; an anchoring assembly that may be coupled to an archwire; and a coiled spring secured at a first end to the bracket and secured at a second end to the anchoring assembly.

In a feature of this aspect, the bracket further includes a spring attachment portion to which the coiled spring is secured at its first end. In further features, the spring attachment portion includes a rigid loop extending from the button or pad; the first end of the spring extends through the loop; the first end of the spring is welded to a main portion of the button or pad; the first end of the spring is welded to a main portion of the button or pad on both sides of the loop; a ball or other body is formed at the first end of the spring so as to prevent the spring from being withdrawn from the loop; the rigid loop is a first rigid loop, and wherein the spring attachment portion includes a second rigid loop through which the first end of the spring also extends; the spring attachment portion is connected to the button or pad via a standoff portion; the spring attachment portion is parallel to a main portion of the button or pad; the standoff portion extends perpendicularly from a main portion of the button or pad; the standoff portion extends perpendicularly from the spring attachment portion; the standoff portion includes a relief opening along at least one edge thereof to facilitate manufacture; the spring attachment portion is co-planar with, and extends away from, a main portion of the button or pad; the spring attachment portion includes at least one slot through which the spring is routed; the at least one slot includes a pair of separate slot openings; the at least one slot includes a pair of conjoined slot openings; the conjoined slot openings are partially separated by a peg; the spring is threaded through the at least one slot; the coil spring is threaded through at least one slot in the spring attachment portion; the coil spring is threaded through a pair of slots in the spring attachment portion; and/or the coil spring defines a longitudinal axis, and wherein the longitudinal axis of the coil spring is co-planar with the spring attachment portion.

In another feature of this aspect, the coil spring defines a longitudinal axis, and wherein the longitudinal axis of the coil spring is co-planar with a main portion of the button or pad; the anchoring assembly includes an anchoring feature and a spring attachment portion; the spring attachment portion is connected to the anchoring feature via a standoff portion; the spring attachment portion includes at least one slot through which the spring is routed; the anchoring feature includes a hook; the hook is a round hook; the hook is a rectangular hook; the rectangular hook includes an angled tip; and/or the angled tip may be crimped around the archwire.

Broadly defined, the present invention according to another aspect is an orthodontic device for effecting movement of an impacted or malpositioned tooth, including: a bracket including a button or pad that is bondable to an impacted or malpositioned tooth and a distinct spring attachment portion to which the spring is secured; an anchoring assembly that may be coupled to an archwire; and a spring secured at a first end to the spring attachment portion of the bracket and secured at a second end to the anchoring assembly.

In a feature of this aspect, the spring attachment portion includes a rigid loop extending from the button or pad. In further features, the first end of the spring extends through the loop; the first end of the spring is welded to a main portion of the button or pad; the first end of the spring is welded to a main portion of the button or pad on both sides of the loop; a ball or other body is formed at the first end of the spring so as to prevent the spring from being withdrawn from the loop; and/or the rigid loop is a first rigid loop, and wherein the spring attachment portion includes a second rigid loop through which the first end of the spring also extends.

In another feature of this aspect, the spring attachment portion is connected to the button or pad via a standoff portion. In further features, the spring attachment portion is parallel to a main portion of the button or pad; the standoff portion extends perpendicularly from a main portion of the button or pad; the standoff portion extends perpendicularly from the spring attachment portion; the standoff portion includes a relief opening along at least one edge thereof to facilitate manufacture; and/or the spring attachment portion is co-planar with, and extends away from, a main portion of the button or pad.

In another feature of this aspect, the spring attachment portion includes at least one slot through which the spring is routed. In further features, the at least one slot includes a pair of separate slot openings; the at least one slot includes a pair of conjoined slot openings; the conjoined slot openings are partially separated by a peg; and/or the spring is threaded through the at least one slot.

In another feature of this aspect, the spring is a coil spring. In further features, the coil spring is threaded through at least one slot in the spring attachment portion; the coil spring is threaded through a pair of slots in the spring attachment portion; the coil spring defines a longitudinal axis, and wherein the longitudinal axis of the coil spring is co-planar with the spring attachment portion; and/or the coil spring defines a longitudinal axis, and wherein the longitudinal axis of the coil spring is co-planar with a main portion of the button or pad.

In another feature of this aspect, the anchoring assembly includes an anchoring feature and a spring attachment portion. In further features, the spring attachment portion of the anchoring assembly is connected to the anchoring feature via a standoff portion; the spring attachment portion of the anchoring assembly includes at least one slot through which the spring is routed; the anchoring feature includes a hook; the hook is a round hook; the hook is a rectangular hook; the rectangular hook includes an angled tip; and/or the angled tip may be crimped around the archwire.

Broadly defined, the present invention according to another aspect is a method of using an orthodontic device to effect movement of an impacted or malpositioned tooth, including: providing an orthodontic device, the orthodontic device including a bracket, a coiled spring, and an anchoring assembly; bonding the bracket to an impacted or malpositioned tooth; connecting a first end of the spring to a first spring attachment portion supported by the bracket; connecting a second end of the spring to a second spring attachment portion supported by the anchoring assembly; and coupling the anchoring assembly to a second orthodontic device that is installed in the patient's mouth.

In a feature of this aspect, the method further includes a step, prior to the bonding step, of surgically opening gum tissue of a patient to reveal the impacted or malpositioned tooth.

In another feature of this aspect, the bracket includes a bondable metal pad or button and the bonding step includes bonding the bondable metal pad or button to the impacted or malpositioned tooth. In further features, the first spring attachment portion includes at least one slot through which the spring is routed; and/or the second spring attachment portion includes at least one slot through which the spring is routed.

In another feature of this aspect, the anchoring feature includes a hook. In further features, the step of coupling the anchoring assembly to an orthodontic device includes coupling the hook to an archwire; and/or the method further includes a step of crimping the hook around the archwire Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
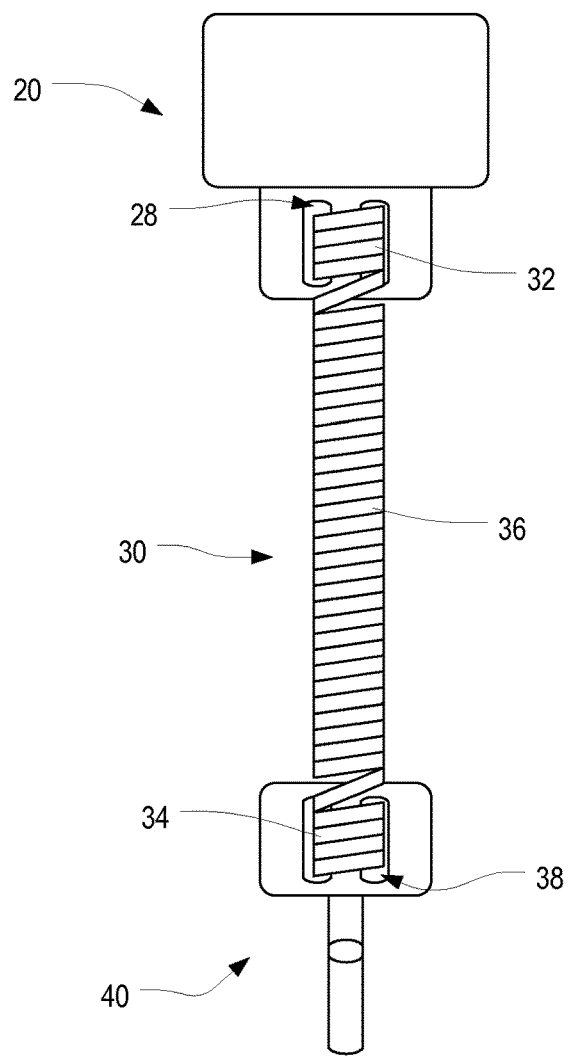
FIG. 1 is a front view of an orthodontic device for exposure of impacted teeth in accordance with one or more preferred embodiments of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

Figure 2:
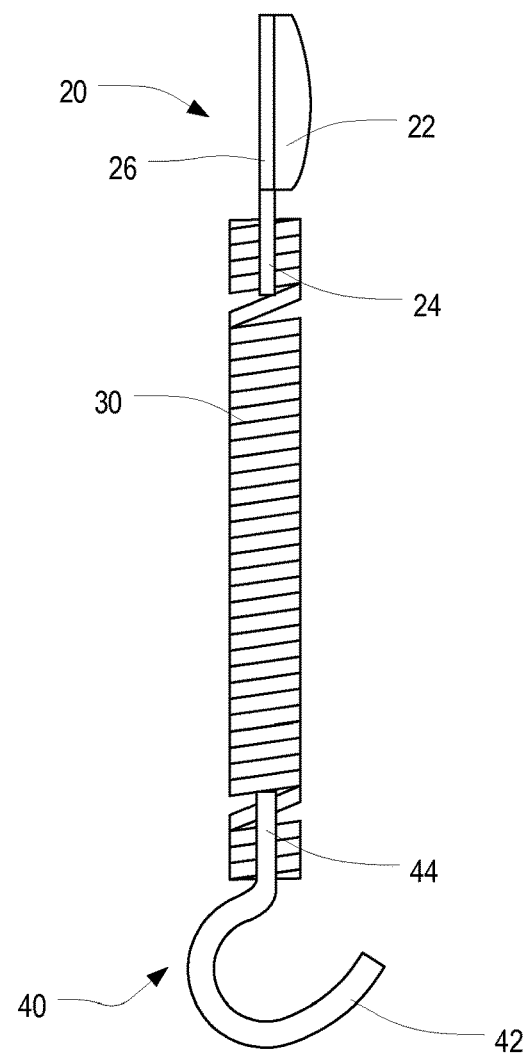
FIG. 2 is a side view of the orthodontic device of FIG. 1.

FIGS. 1 and 2 are a front view and a side view, respectively, of an orthodontic device 10 for exposure of impacted teeth in accordance with one or more preferred embodiments of the present invention. As shown therein, the orthodontic device 10 includes a bondable bracket 20, a spring 30 (shown in its inactive state) connected at one end to the bracket 20, and an anchoring assembly 40 connected to the other end of the spring 30. Each of these is described in greater detail herein.

Figure 3A:
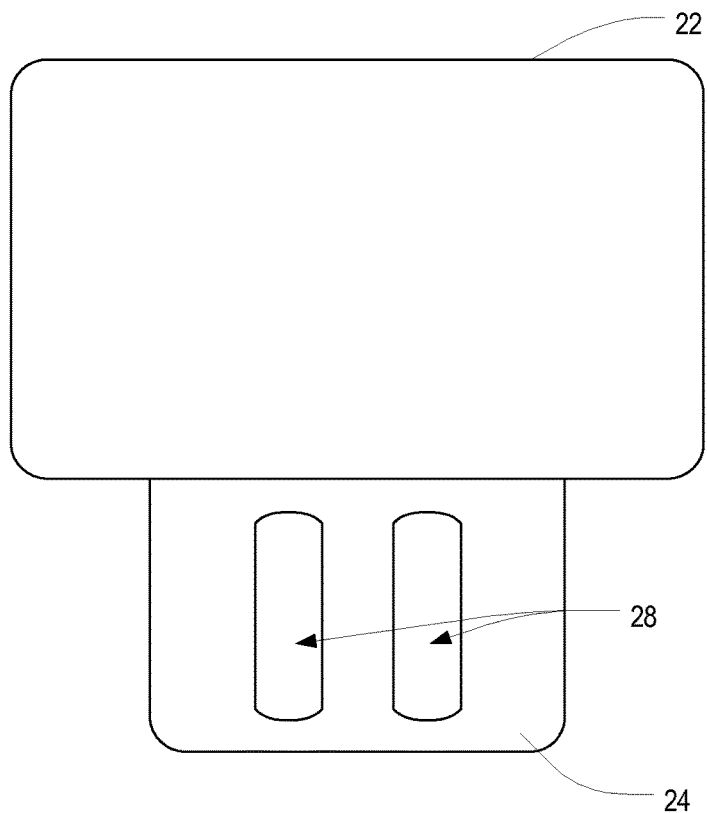
FIGS. 3A and 3B are front views, with and without contemplated dimensions, of the bondable pad of FIGS. 1 and 2.
Figure 3B:
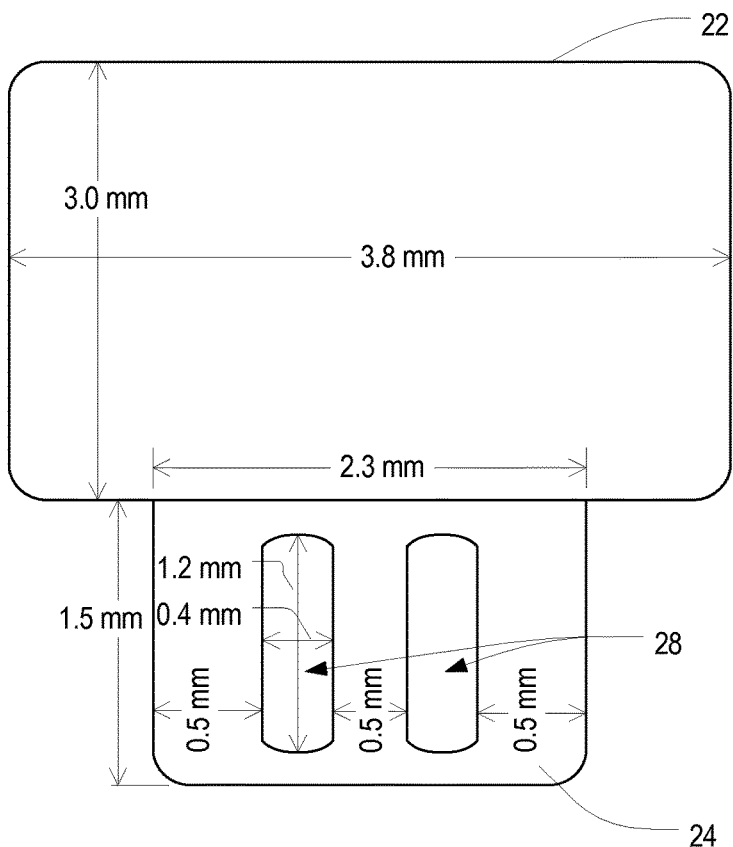
Figure 4:
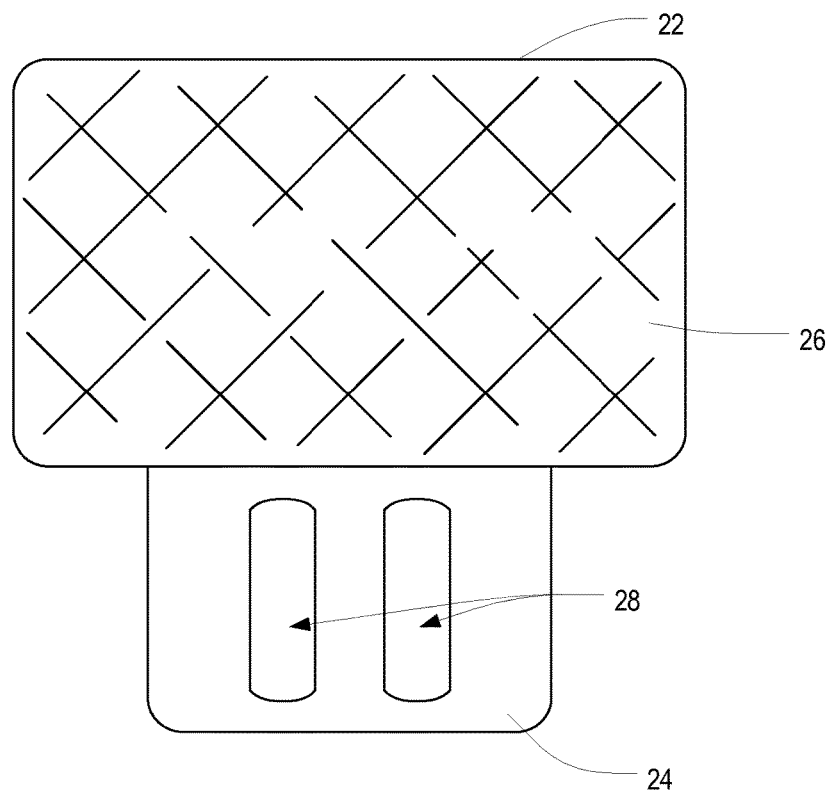
FIG. 4 is a rear view of the bondable pad of FIGS. 3A and 3B.
Figure 5:
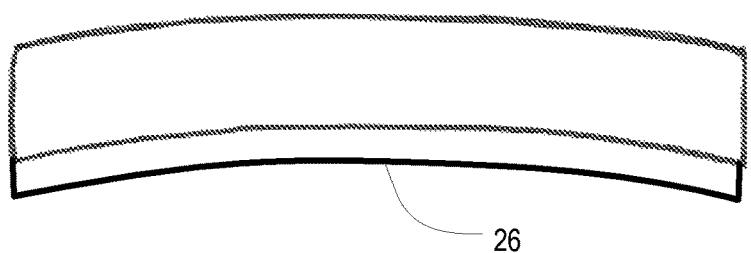
FIG. 5 is a top view of the bondable bracket of FIGS. 1 and 2.
Figure 6:
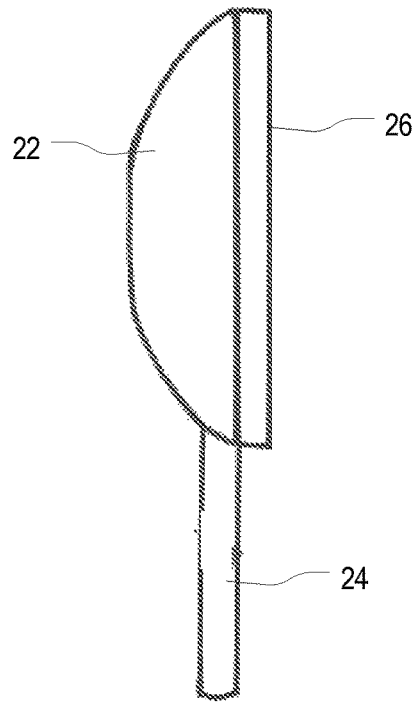
FIG. 6 is a side view of the bondable bracket of FIG. 5.

FIGS. 3A and 3B are front views, with and without contemplated dimensions, of the bondable bracket 20 of FIGS. 1 and 2; and FIGS. 4, 5, and 6 are a rear view, a top view, and a side view, respectively, of the bondable bracket 20 of FIGS. 3A and 3B. The bracket 20 includes a bondable metal pad or button 22 and a spring attachment portion 24. The pad or button 22 may be bonded to an impacted tooth or other tooth of interest using a conventional dental or orthodontic bonding adhesive. The rear of the pad or button 22 may include a metal retentive mesh 26 where the bonding adhesive (not shown) may be placed. In at least some embodiments, the pad or button 22 is curved so as to better fit the contours of the tooth to which it is to be bonded. Such curvature may be side to side, top to bottom, or both, and different amounts of curvature may be supplied on different bondable brackets 20 so as to facilitate selection of the proper degree of curvature. The spring attachment portion 24 may include one or more features for attaching or connecting an end of a spring thereto. For example, in the illustrated embodiment, the spring attachment portion 24 includes a pair of slot openings 28 for receiving one or more loops or coils of a coiled spring. In at least some embodiments, the bracket 20, including the mesh 26, are produced from stainless steel.

Dimensions of one particular contemplated embodiment are shown in FIG. 3B. The bondable bracket 20 may be 4.5 mm tall. The pad or button 22 may be 3.0 mm tall, 3.8 mm wide, and 0.3 mm thick. The spring attachment portion 24 may be 1.5 mm tall, 2.3 mm wide and 0.3-0.4 mm thick. The slot openings 28 may be 1.2 mm long and 0.4 mm wide, and may be spaced from each other and from the sides of the spring attachment portion 24 by 0.5 mm.

Figure 7:
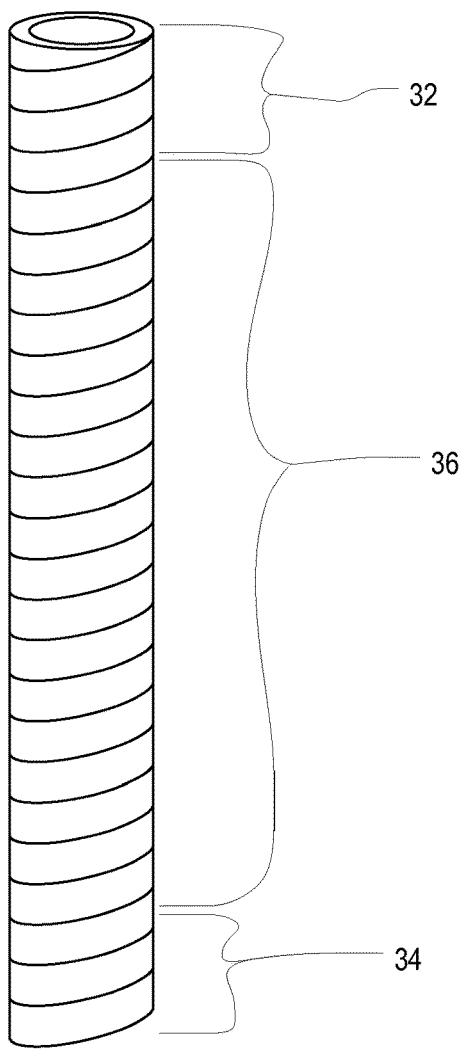
FIG. 7 is a side view of the spring of FIGS. 1 and 2, shown in an inactive state.

FIG. 7 is a side view of the spring 30 of FIGS. 1 and 2, shown in an inactive state. The spring 30 includes a first end 32, a second end 34, and a middle section 36. The first end 32 connects to the bondable bracket 20 and the second end 34 connects to the anchoring assembly 40. In the illustrated embodiment, multiple coils of the first spring end 32 are wound through the slot openings 28 in the bondable bracket 20 and multiple coils of the second spring end 34 are wound through the slot openings 38 in the anchoring assembly 40. The middle spring section 36 is preferably between 3 and 13 mm in length, and is more preferably between 5 and 11 mm in length. In one contemplated embodiment, the middle spring section 36 is 5 mm in length. In another contemplated embodiment, the middle spring section 36 is 8 mm in length. In another contemplated embodiment, the middle spring section 36 is 11 mm in length. Also, in one contemplated embodiment, the first end 32 and the second end 34 are each approximately 0.5 mm in length. The diameter of the spring is preferably between 1.0 mm and 1.5 mm, and in a particular contemplated embodiment is 1.3 mm in diameter.

In at least some embodiments, the spring 30 is preferably produced from some sort of superelastic metal, such as nickel-titanium ("NiTi" or "nitinol"), copper nitinol, alloys thereof, or the like. Furthermore, in at least some embodiments, the middle section 36 of the spring 30 is shaped in the form of a non-planar, helical coil spring that can be stretched or "activated" to a greater length. In at least some of these embodiments, the spring exerts approximately 150-250 g of pull force as it collapses from its stretched or "active" state back to its inactive state.

Figure 8A:
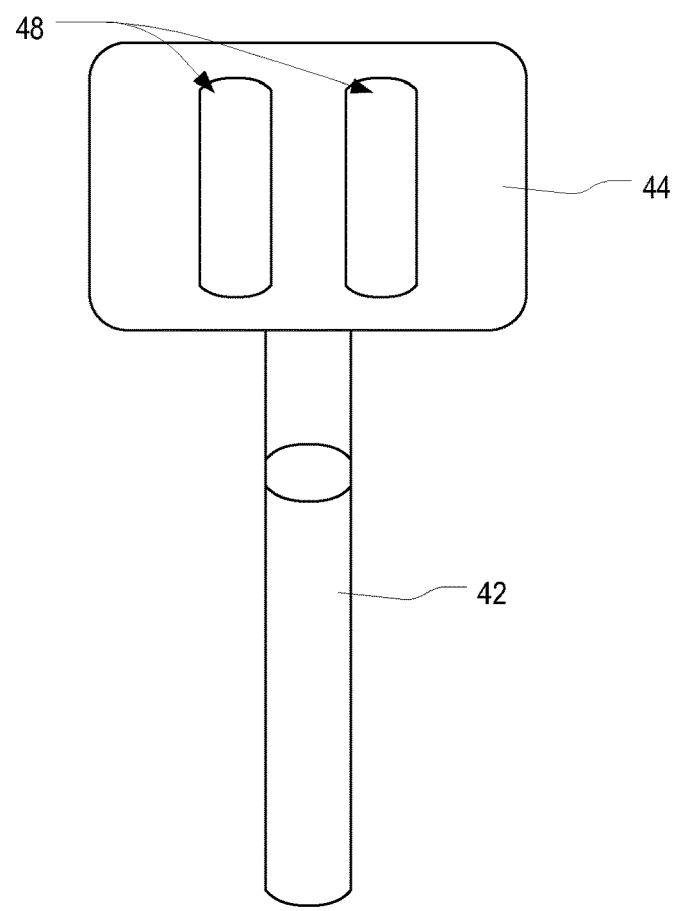
FIGS. 8A and 8B are front views, with and without contemplated dimensions, of the anchoring assembly of FIGS. 1 and 2.
Figure 8B:
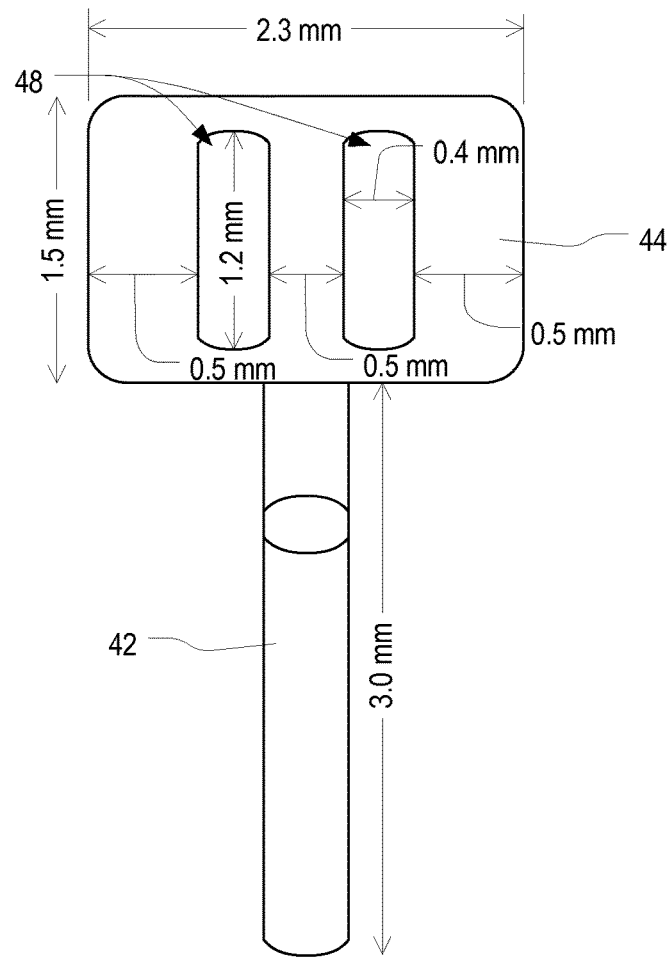

FIGS. 8A and 8B are front views, with and without contemplated dimensions, of the anchoring assembly 40 of FIGS. 1 and 2, and FIGS. 9A and 9B are side views, with and without contemplated dimensions, of the anchoring assembly 40 of FIGS. 8A and 8B. The anchoring assembly 40 includes an anchoring feature 42 and a spring attachment portion 44. In the illustrated embodiment, the anchoring feature 42 is a hook, but in some embodiments, the anchoring feature 42 may include a clamp or other fastening device. The hook or other anchoring feature 42 may be anchored to an orthodontic archwire 98 or the like as described elsewhere herein. The spring attachment portion 44 may include one or more features for attaching or connecting an end of a spring thereto. For example, in the illustrated embodiment, the spring attachment portion 44 includes a pair of slot openings 48 for receiving one or more loops or coils of a coiled spring. The attachment features may be similar to those on the bondable bracket 20, or they may be different. In at least some embodiments, the anchoring assembly 40 is produced from stainless steel.

Figure 9A:
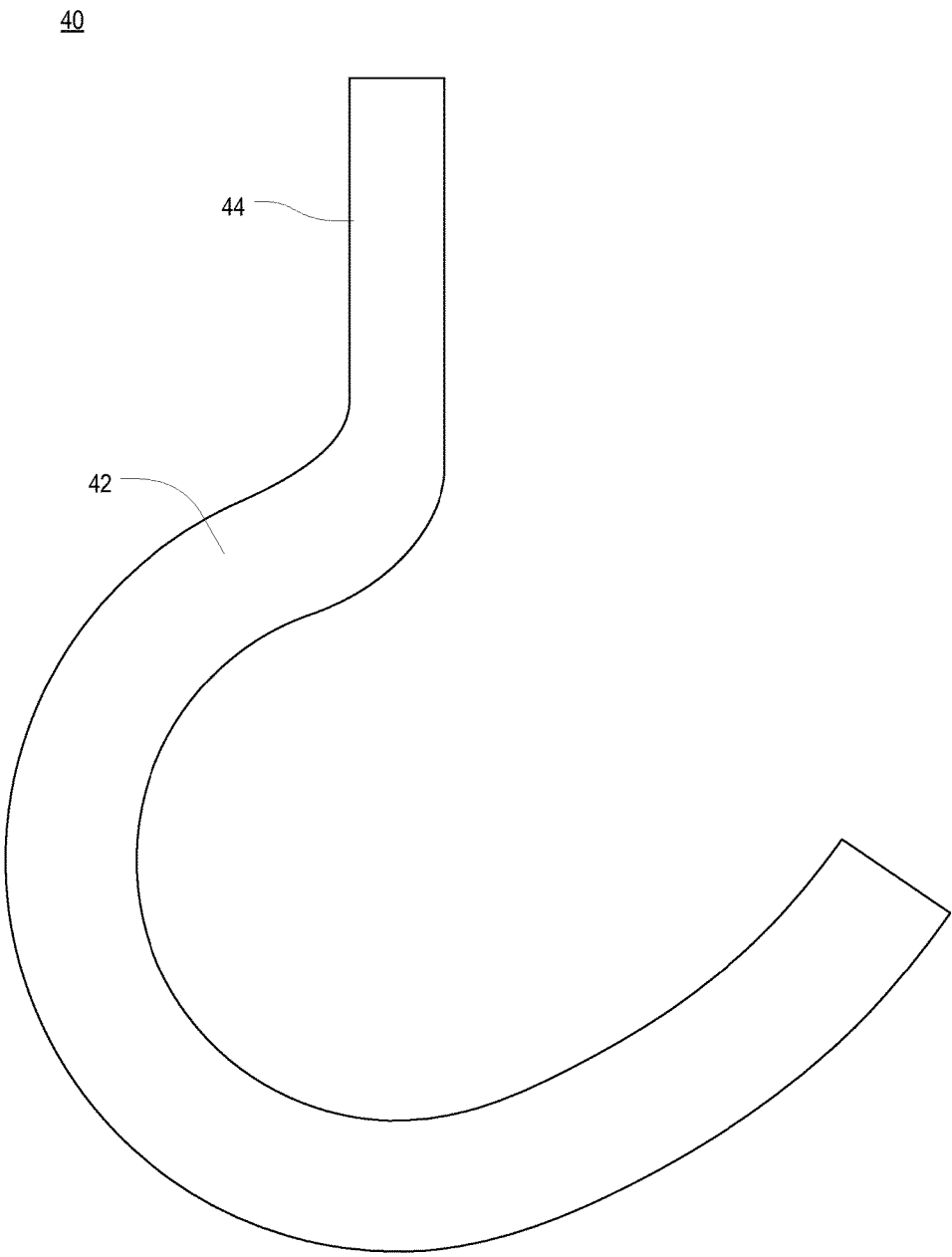
FIGS. 9A and 9B are side views, with and without contemplated dimensions, of the anchoring assembly of FIGS. 8A and 8B.
Figure 9B:
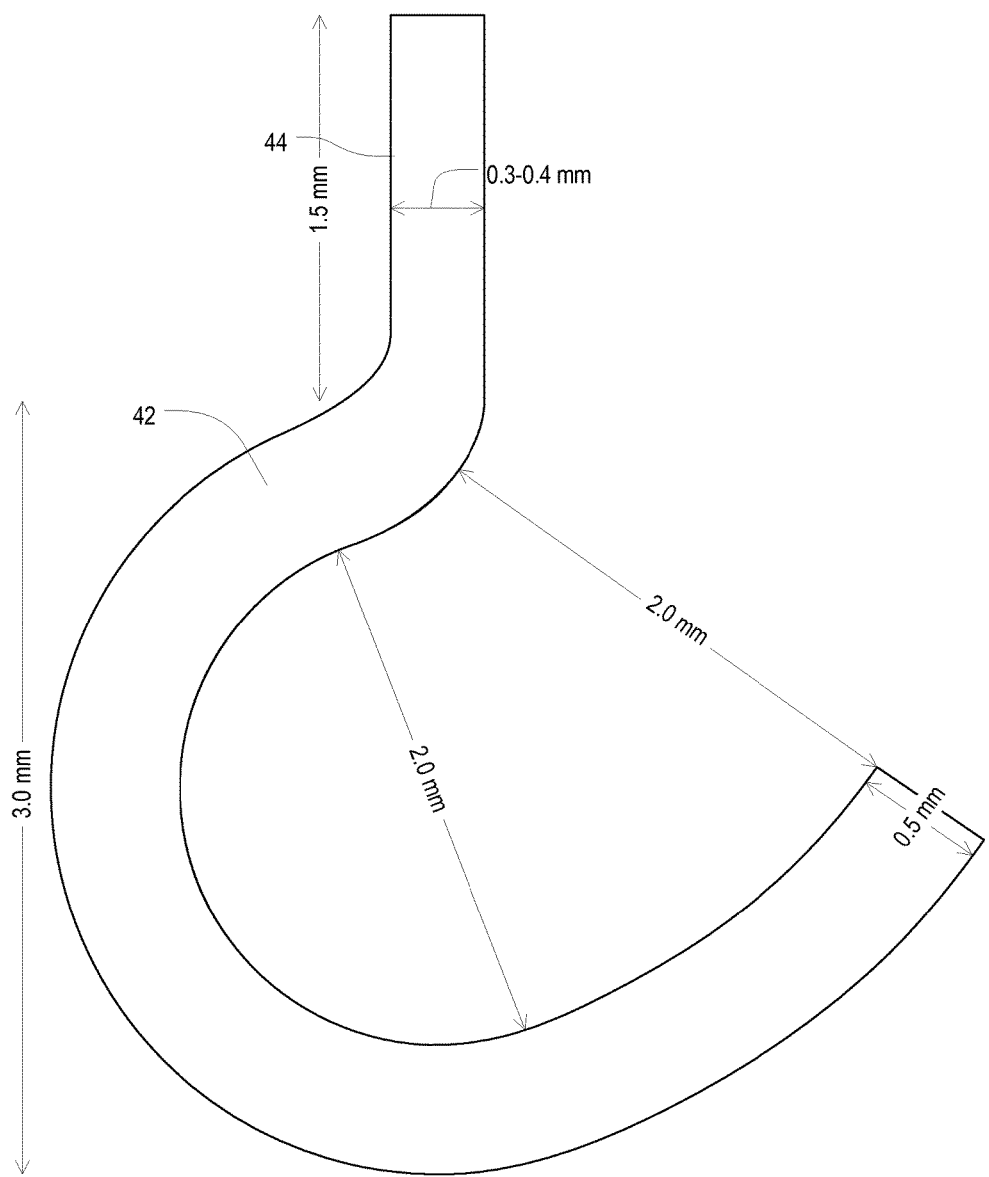

Dimensions of one particular contemplated embodiment are shown in FIGS. 8B and 9B. The anchoring assembly 40 may be 4.5 mm tall. The spring attachment portion 44 may be 1.5 mm tall, 2.3 wide, and 0.3-0.4 mm thick. The anchoring feature 42 may be 3.0 mm tall, 0.5 mm in diameter, and may create a hook having an internal diameter of 2.0 mm and an opening at the end of 2.0 mm. The slot openings 48 may be 1.2 mm long and 0.4 mm wide, and may be spaced from each other and from the sides of the spring attachment portion 24 by 0.5 mm.

Figure 10A:
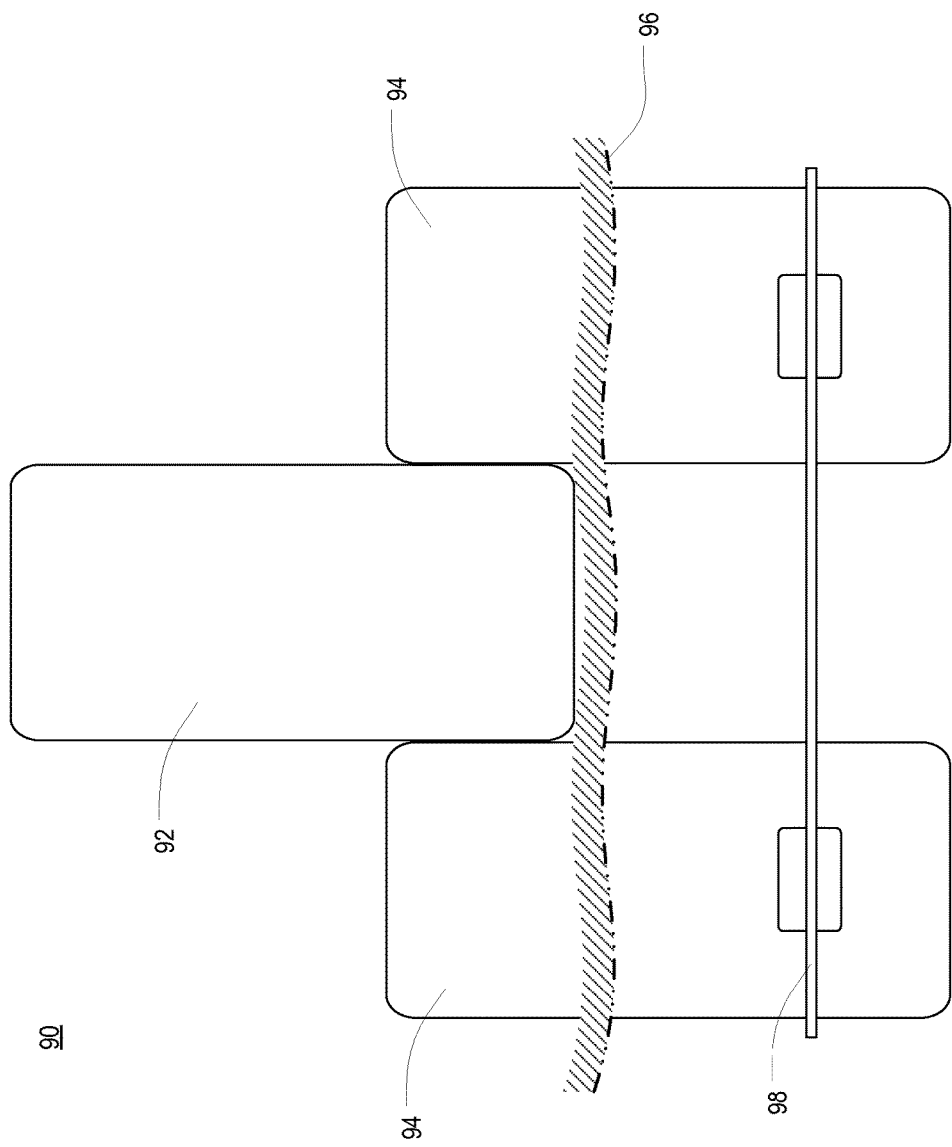
FIGS. 10A-10E are a series of schematic illustrations of the device of FIGS. 1 and 2 in use in a patient's mouth.
Figure 10B:
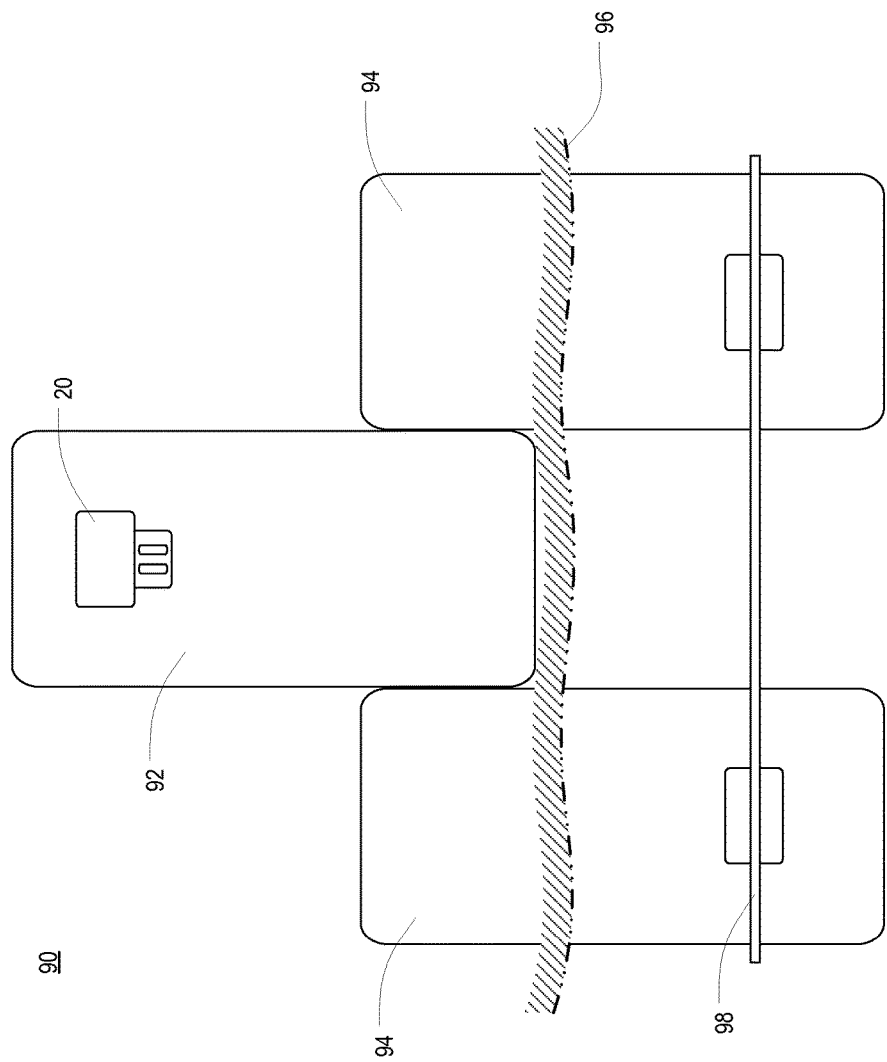
Figure 10C:
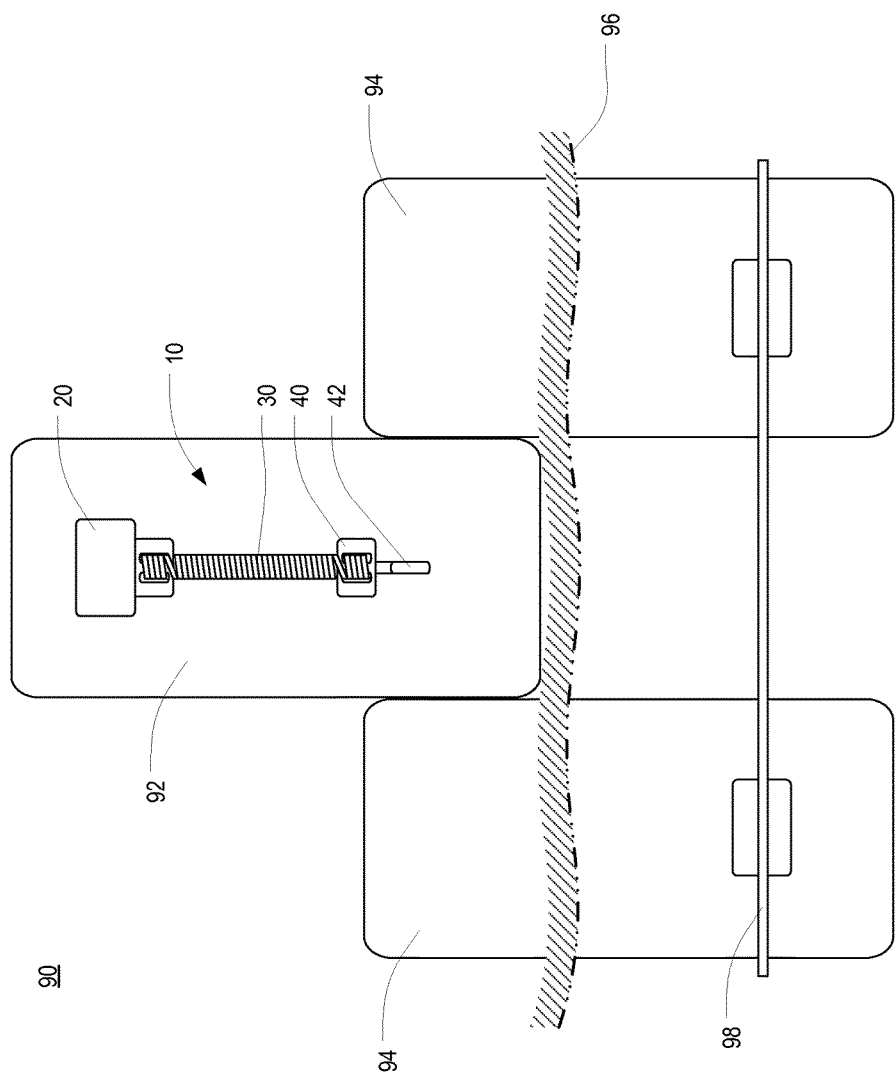

The orthodontic device 10 may be used to quickly adjust the position, location, and/or orientation of an impacted tooth. In this regard, FIGS. 10A-10E are a series of schematic illustrations of the device 10 of FIGS. 1 and 2 in use in a patient's mouth 90. In FIG. 10A, an impacted tooth 92 is shown as being above the adjacent teeth 94, where it has failed to erupt from the gum tissue 96. It is anticipated that the device 10 may typically be installed during surgery, in which the gum tissue 96 is opened to facilitate access to the impacted tooth 92, but it will be appreciated that in some situations surgery may not be necessary. In FIG. 10B, the bondable bracket 20 is shown installed on the impacted tooth 92, and in FIG. 10C, the spring 30 and anchoring assembly 40 are shown connected to the bondable bracket 20. (It will be appreciated that in some embodiments, the device 10 may be installed as a single unit, while in some embodiments, the bondable bracket 20 may be bonded to the tooth 92 first, and then the spring 30 and anchoring assembly 40 connected afterward.)

Figure 10D:
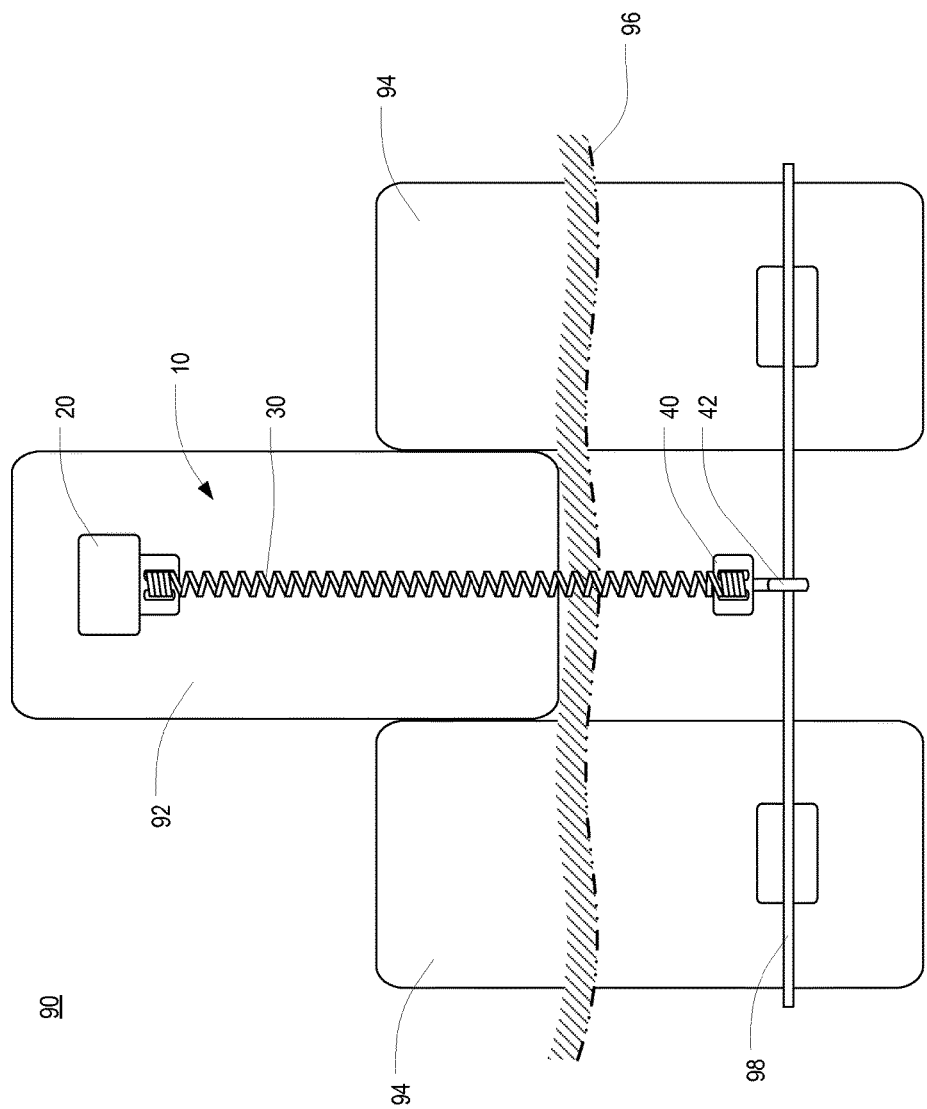
Figure 10E:
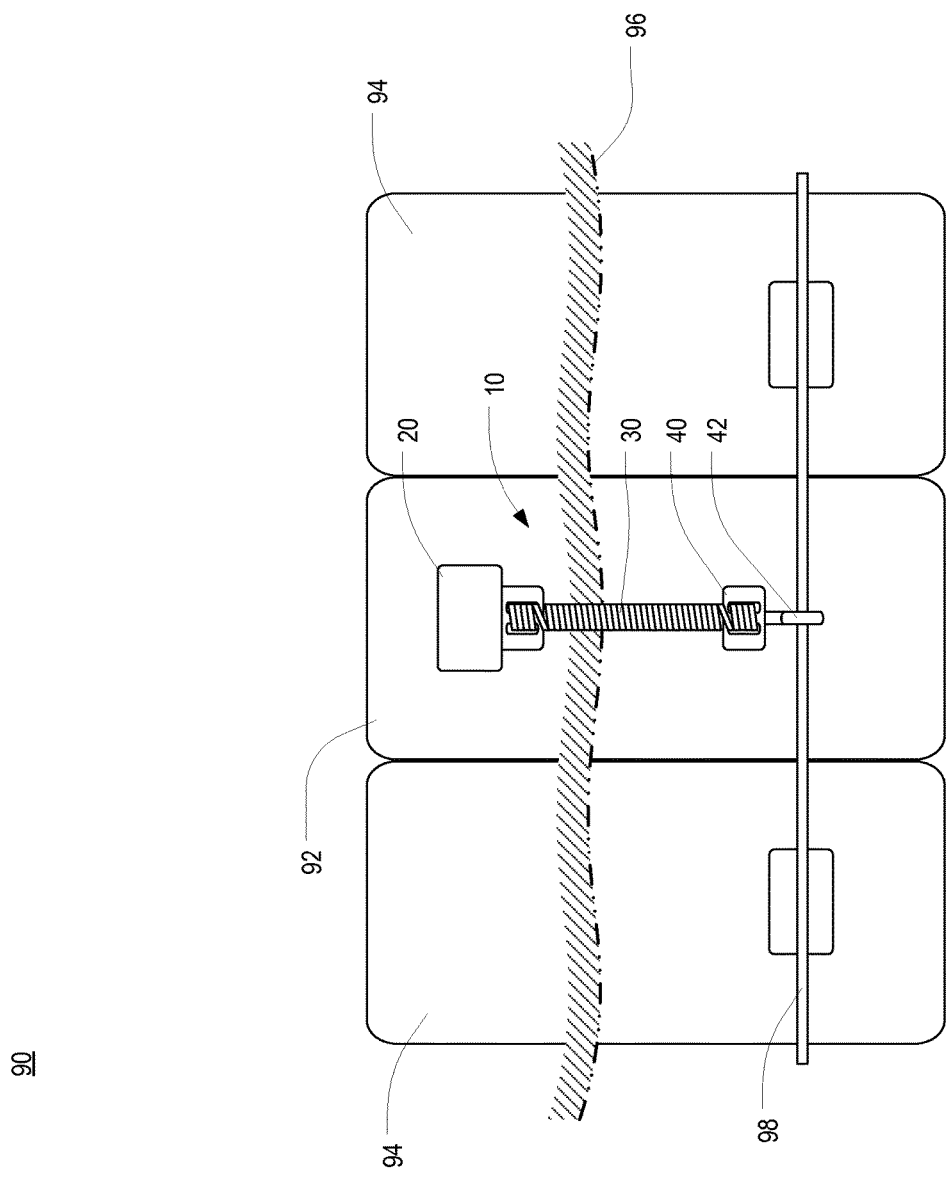

With the bondable bracket 20 bonded to the involved tooth 92, the spring 30 is "activated" or stretched, and the anchoring assembly 40 is attached to the orthodontic archwire 98, as shown in FIG. 10D. With the spring activated, the spring 30 applies a relatively constant and orthodontically-friendly force to the involved tooth 92 over a longer period of time when compared to traditional methods. It is thus potentially possible to carry out surgery on a particular patient a fewer number of times, to make adjustments less frequently, and to reduce the overall amount of time that is required to force eruption of the impacted tooth 92 through the gum tissue 96 and to bring it into a proper position between the adjacent teeth 94 as shown in FIG. 10E.

By selecting the shortest possible length of spring 30 that will stretch from the involved tooth 92 to the orthodontic archwire 98 without undergoing permanent deformation, the device 10 will remain active over the longest period of time without the need for adjustment or reactivation by the orthodontist. Ideally, the device 10 would be produced in different "sizes" that differ only in the length of the middle section 36 of the coil spring 30, so that the practitioner could select the appropriate length of device 10 for the particular clinical situation in which it is being used. One contemplated set of sizes includes one size in which the middle spring section 36 is 5 mm in length when in its inactive state, one size in which the middle spring section 36 is 8 mm in length when in its inactive state, and one size in which the middle spring section 36 is 11 mm in length when in its inactive state. If the first and second spring end sections 32,34 are 0.5 mm in length, then the overall length of these three spring sizes would be 6 mm, 9 mm, and 12 mm, respectively.

Figure 11:
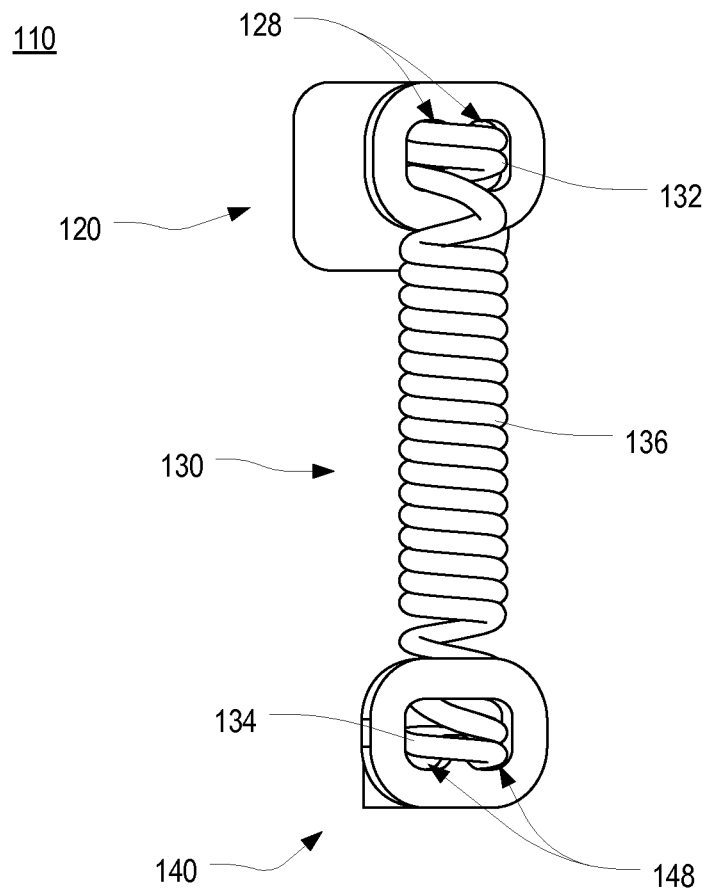
FIG. 11 is a front left view of an orthodontic device, shown in its inactive state, for exposure of impacted teeth in accordance with one or more preferred further embodiments of the present invention.
Figure 12A:
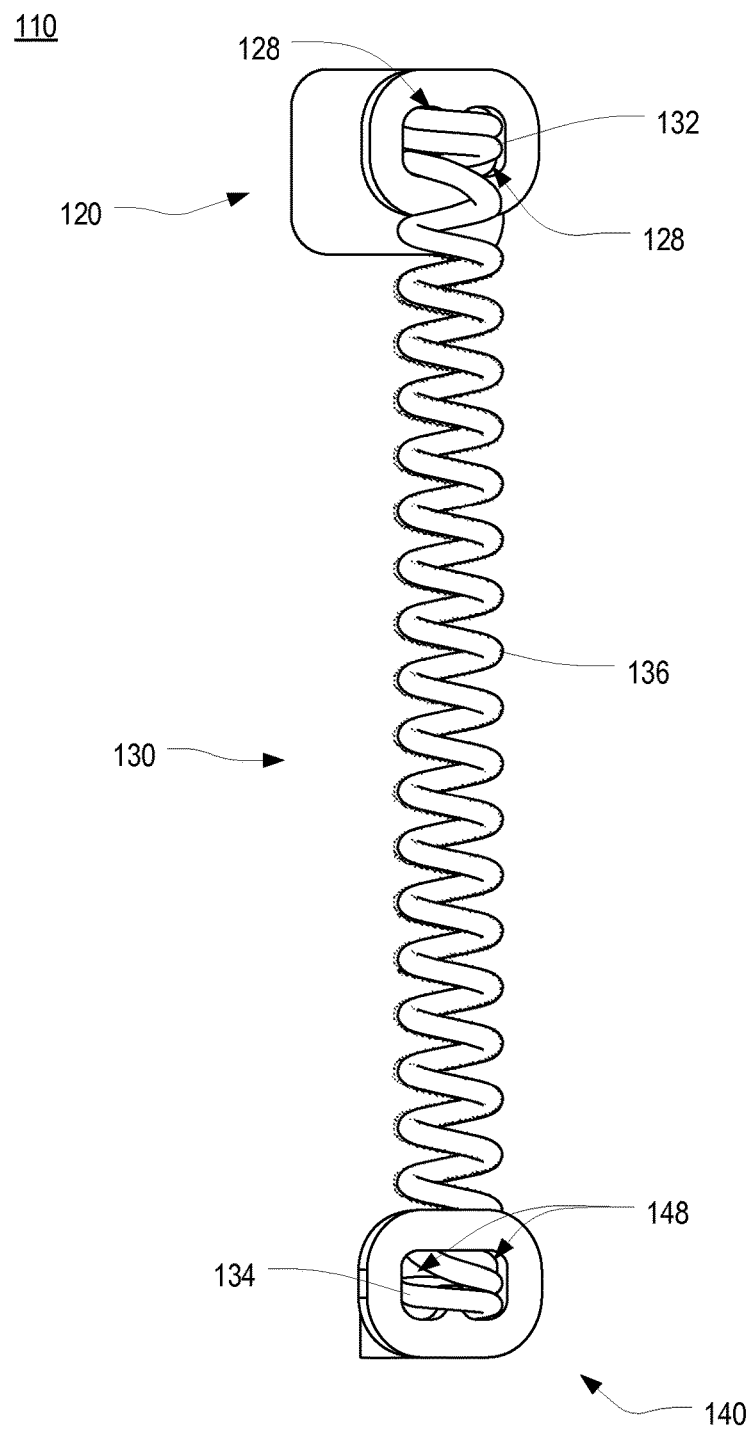
FIGS. 12A and 12B are a front left view and a right side view, respectively, of the orthodontic device of FIG. 11, shown in its stretched or "activated" state.
Figure 12B:
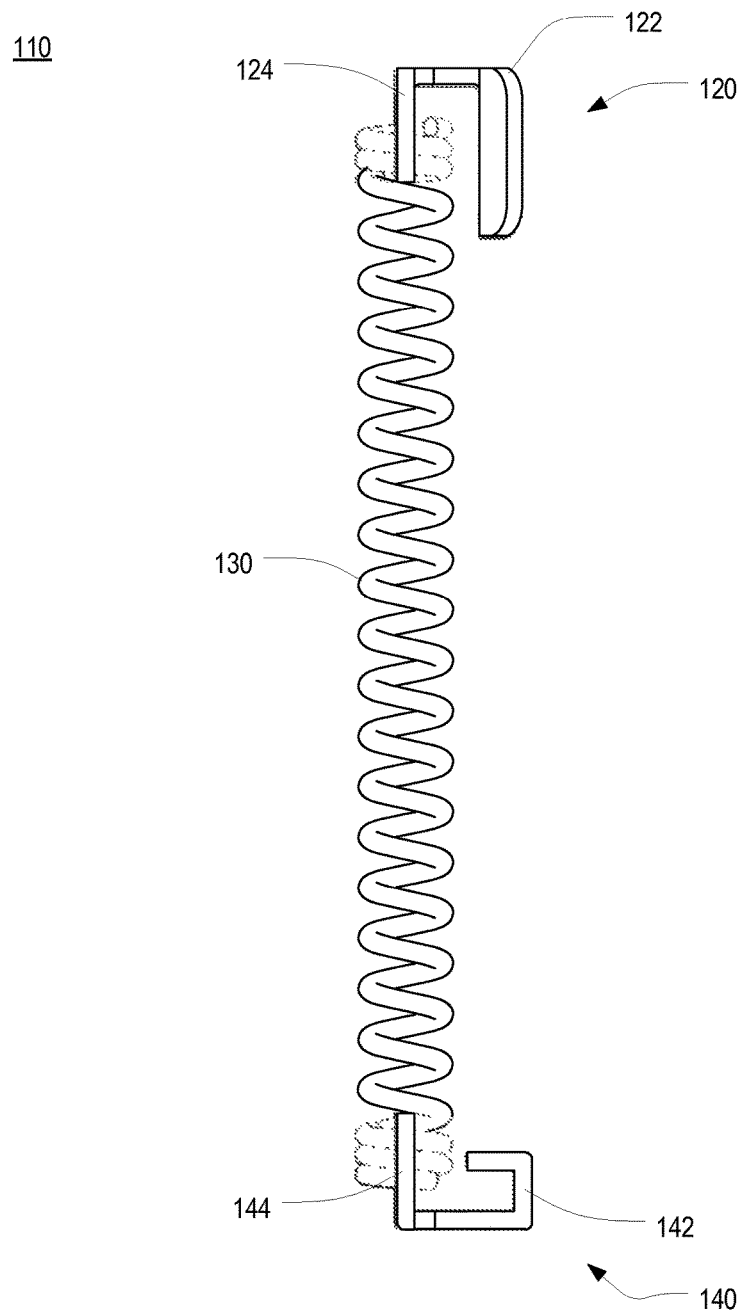

FIG. 11 is a front left view of an orthodontic device 110, shown in its inactive state, for exposure of impacted teeth in accordance with one or more preferred further embodiments of the present invention, while FIGS. 12A and 12B are a front left view and a right side view, respectively, of the orthodontic device 110 of FIG. 11, shown in its stretched or "activated" state. As shown therein, the orthodontic device 110 includes a bondable bracket 120, a spring 130 (shown in its inactive state) connected at one end to the bracket 120, and an anchoring assembly 140 connected to the other end of the spring 130. Each of these is described in greater detail herein.

Figure 13:
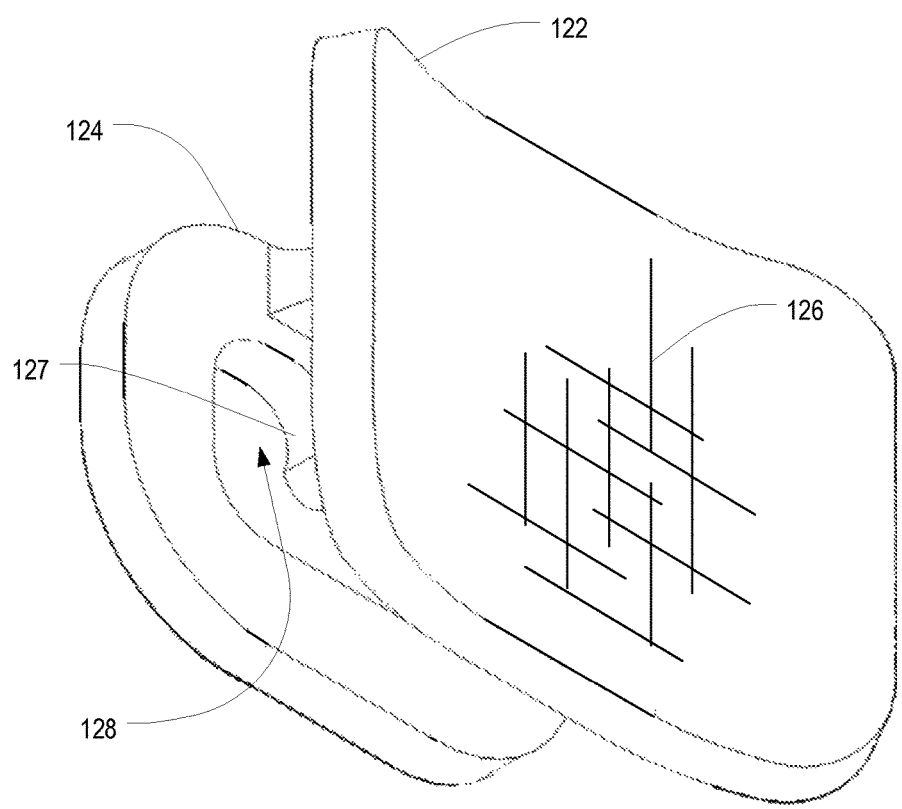
FIG. 13 is a bottom rear orthogonal view of the bondable bracket of FIG. 12B.
Figure 14:
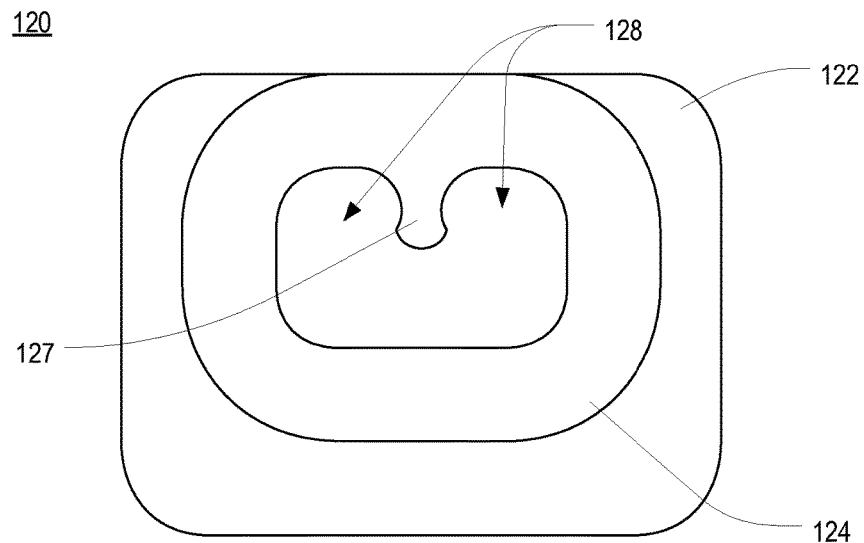
FIG. 14 is a front view of the bondable bracket of FIG. 13.
Figure 15:
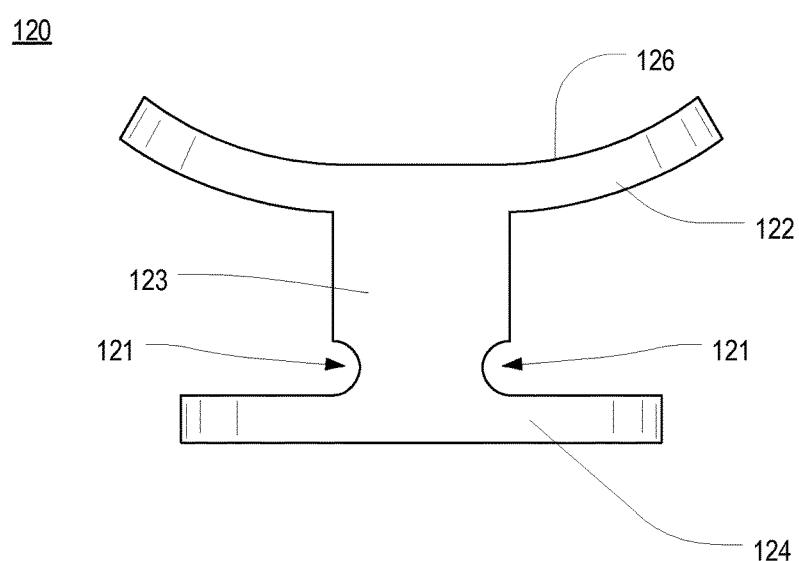
FIG. 15 is a top view of the bondable bracket of FIG. 13.
Figure 16:
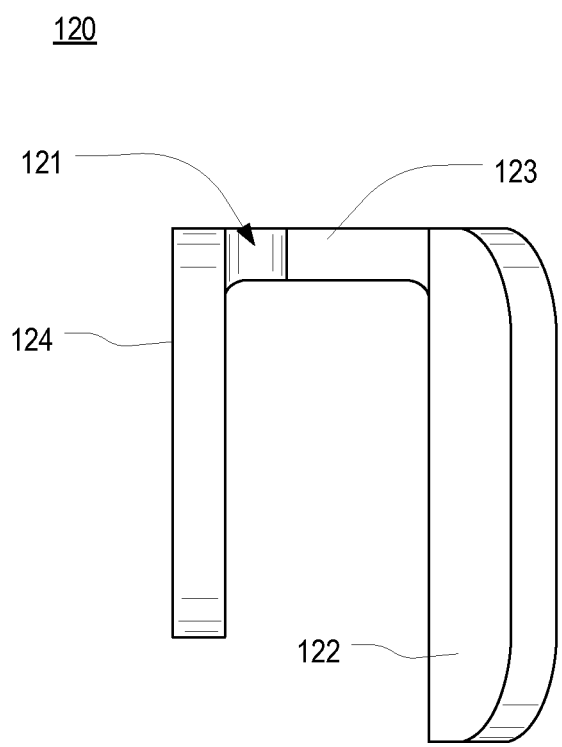
FIG. 16 is a right side view of the bondable bracket of FIG. 13.

FIG. 13 is a bottom rear orthogonal view of the bondable bracket 120 of FIG. 12B; and FIGS. 14, 15, and 16 are a front view, a top view, and a right side view, respectively, of the bondable bracket 120 of FIG. 13. The bracket 120 includes a bondable metal pad or button 122 and a spring attachment portion 124. The pad or button 122 may be bonded to an impacted tooth or other tooth of interest using a conventional dental or orthodontic bonding adhesive. The rear of the pad or button 122 may include a metal retentive mesh 126 (representatively illustrated in FIG. 13) where the bonding adhesive (not shown) may be placed. In at least some embodiments, the pad or button 122 is curved so as to better fit the contours of the tooth 92 to which it is to be bonded. Such curvature may be side to side, top to bottom, or both, and different amounts of curvature may be supplied on different bondable brackets 120 so as to facilitate selection of the proper degree of curvature. The spring attachment portion 124 may include one or more features for attaching or connecting an end of a spring thereto. For example, in the illustrated embodiment, the spring attachment portion 124 includes a pair of conjoined slot openings 128, separated by a peg 127, for receiving one or more loops or coils of a coiled spring. The bracket 120 also includes a standoff portion 123 extending perpendicularly between the pad or button 122 and the spring attachment portion 124 to position the spring attachment features in front of the pad or button 122. As shown in FIGS. 15 and 16, relief openings 121 may optionally be provided in the standoff portion 123 near the attachment portion 124 to facilitate manufacturing.

Dimensions of one particular contemplated embodiment of the bondable bracket 120 are as follows. The bondable bracket 120 may be 4.5 mm tall. The pad or button 122 may be 3.0 mm tall, 3.8 mm wide, and 0.3 mm thick. The spring attachment portion 124 may be 1.5 mm tall, 2.3 mm wide and 0.3-0.4 mm thick. The conjoined slot openings 128 may be 1.2 mm long and 0.4 mm wide, and their main portions may be spaced from each other and from the sides of the spring attachment portion 124 by 0.5 mm.

Figure 17:
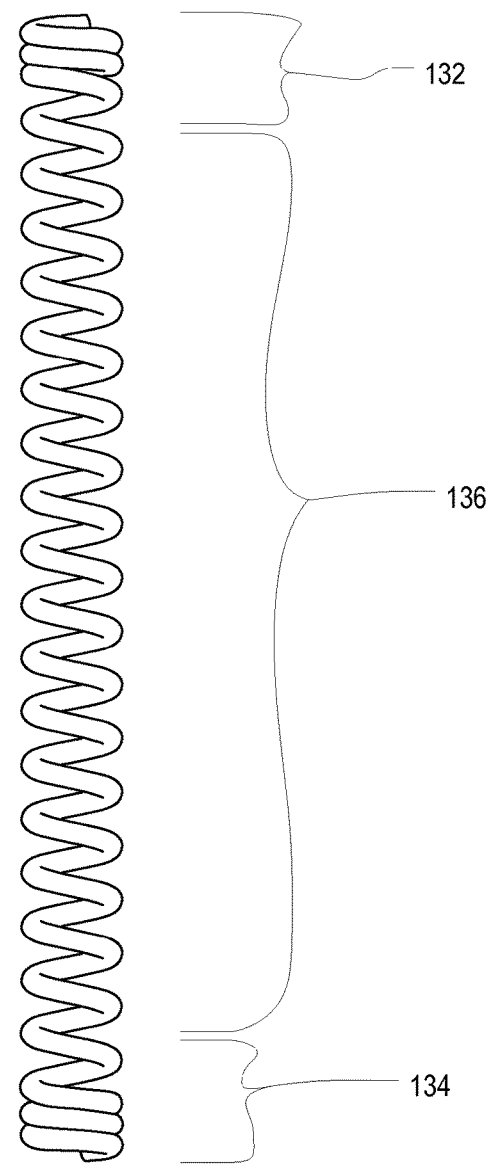
FIG. 17 is a side view of the spring of FIGS. 12A and 12B, shown in its active state.

FIG. 17 is a side view of the spring 130 of FIGS. 12A and 12B, shown in its active state. The spring 130 includes a first end 132, a second end 134, and a middle section 136. The first end 132 connects to the bondable bracket 120 and the second end 134 connects to the anchoring assembly 140. In the illustrated embodiment, multiple coils of the first spring end 132 are wound through the conjoined slot openings 128 in the bondable bracket 120 and multiple coils of the second spring end 134 are wound through conjoined slot openings 148 in the anchoring assembly 140.

In at least some embodiments, the spring 130 is preferably produced from some sort of superelastic metal, such as nickel-titanium ("NiTi" or "nitinol"), copper nitinol, alloys thereof, or the like. Furthermore, in at least some embodiments, the middle section 136 of the spring 130 is shaped in the form of a non-planar, helical coil spring that can be stretched or "activated" to a greater length. In at least some of these embodiments, the spring exerts approximately 150-200 g of pull force as it collapses from its stretched or "active" state back to its inactive state. In at least some other embodiments, a constant force spring or constant tension spring, made from a flat ribbon or band of steel or the like, that exerts a constant or nearly constant force over its range of motion. In various alternative embodiments, other types of springs may utilized instead, including conical springs (particularly those providing constant or nearly constant forces), clock springs, simple wire springs, and/or the like.

Figure 18:
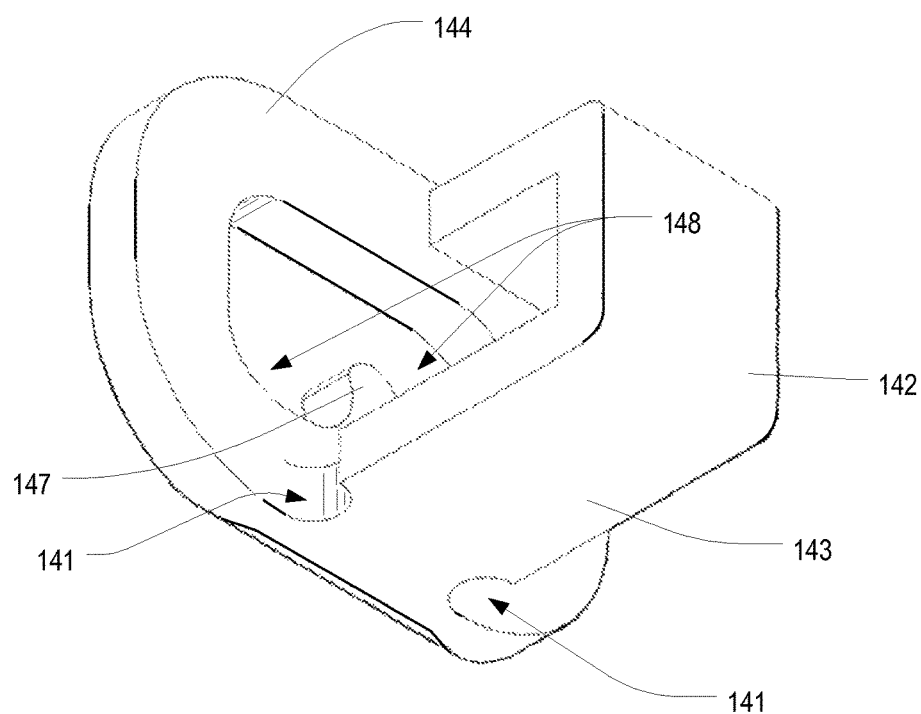
FIG. 18 is a bottom rear orthogonal view of the anchoring assembly of FIG. 12B.
Figure 19:
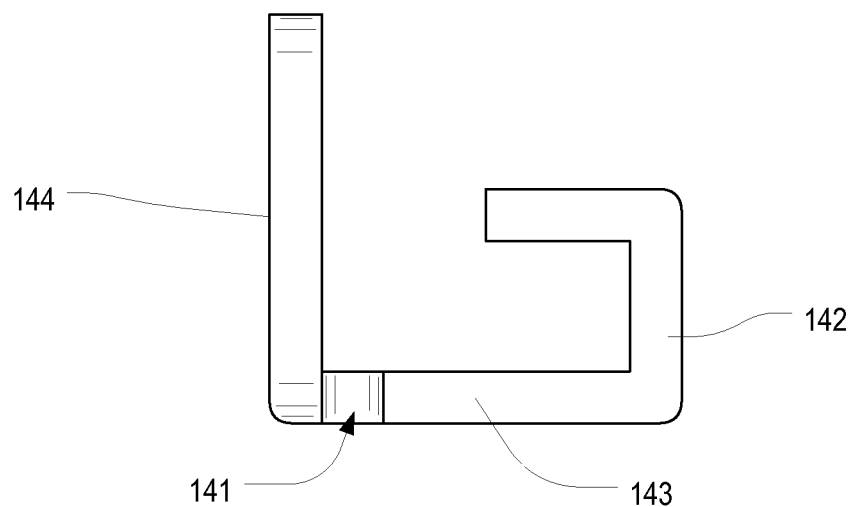
FIG. 19 is a right side view of the anchoring assembly of FIG. 18.

FIG. 18 is a bottom rear orthogonal view of the anchoring assembly 140 of FIG. 12B, and FIG. 19 is a right side view of the anchoring assembly 140 of FIG. 18. The anchoring assembly 140 includes an anchoring feature 142 and a spring attachment portion 144. In the illustrated embodiment, the anchoring feature 142 is a rectangular hook, but in some embodiments, the anchoring feature 142 may include a clamp or other fastening device. The hook or other anchoring feature 142 may be anchored to an orthodontic archwire 98 or the like as described elsewhere herein. The spring attachment portion 144 may include one or more features for attaching or connecting an end of a spring thereto. For example, in the illustrated embodiment, the spring attachment portion 144 includes a pair of conjoined slot openings 148, separated by a peg 147, for receiving one or more loops or coils of a coiled spring. The attachment features may be similar to those on the bondable bracket 120, or they may be different. The anchoring assembly 140 also includes a standoff portion 143 extending perpendicularly between the anchoring feature 142 and the spring attachment portion 144 to position the spring attachment features in front of the anchoring feature 142. As shown in FIGS. 18 and 19, relief openings 141 may optionally be provided in the standoff portion 143 near the attachment portion 144 to facilitate manufacturing.

Dimensions of one particular contemplated embodiment of the anchoring assembly bracket 140 are as follows. The anchoring assembly 40 may be 4.5 mm tall. The spring attachment portion 144 may be 1.5 mm tall, 2.3 wide, and 0.3-0.4 mm thick. The anchoring feature 142 may be 3.0 mm tall, 0.5 mm in diameter, and may create a hook having an internal cross-section of 2.0 mm and an opening at the end of 2.0 mm. The slot openings 148 may be 1.2 mm long and 0.4 mm wide, and may be spaced from each other and from the sides of the spring attachment portion 124 by 0.5 mm.

Figure 20A:
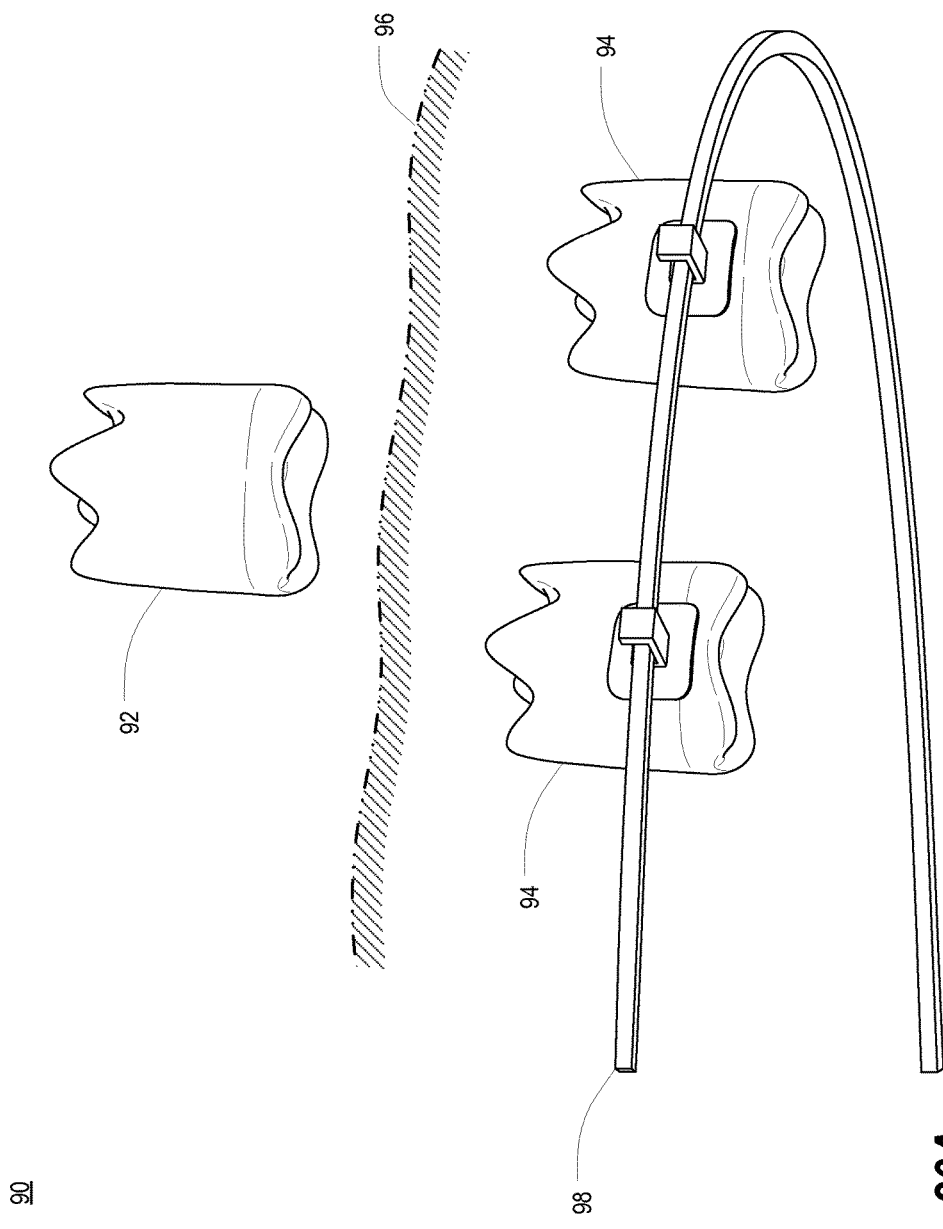
FIGS. 20A-20E are a series of schematic illustrations of the device of FIG. 11 in use in a patient's mouth.
Figure 20B:
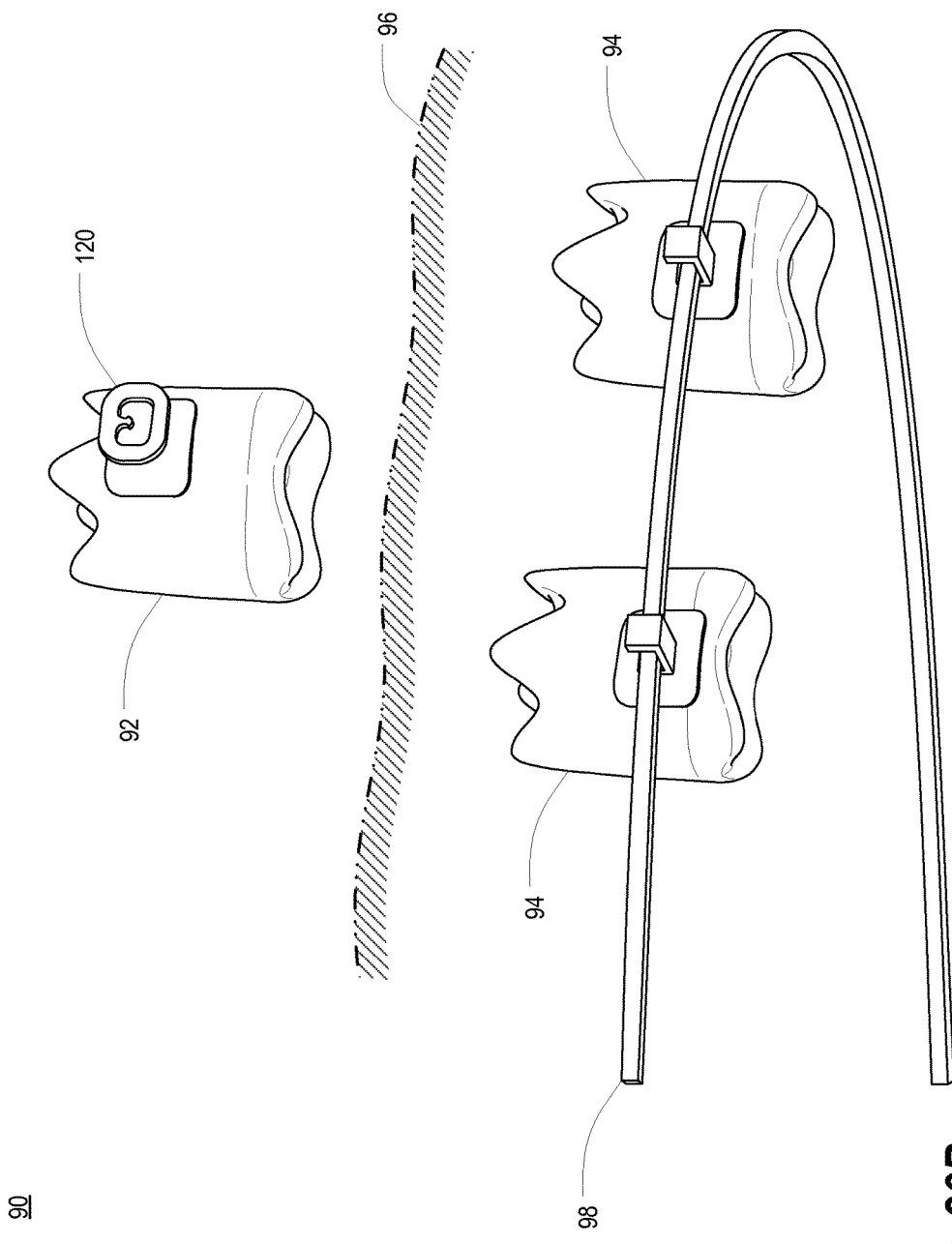
Figure 20C:
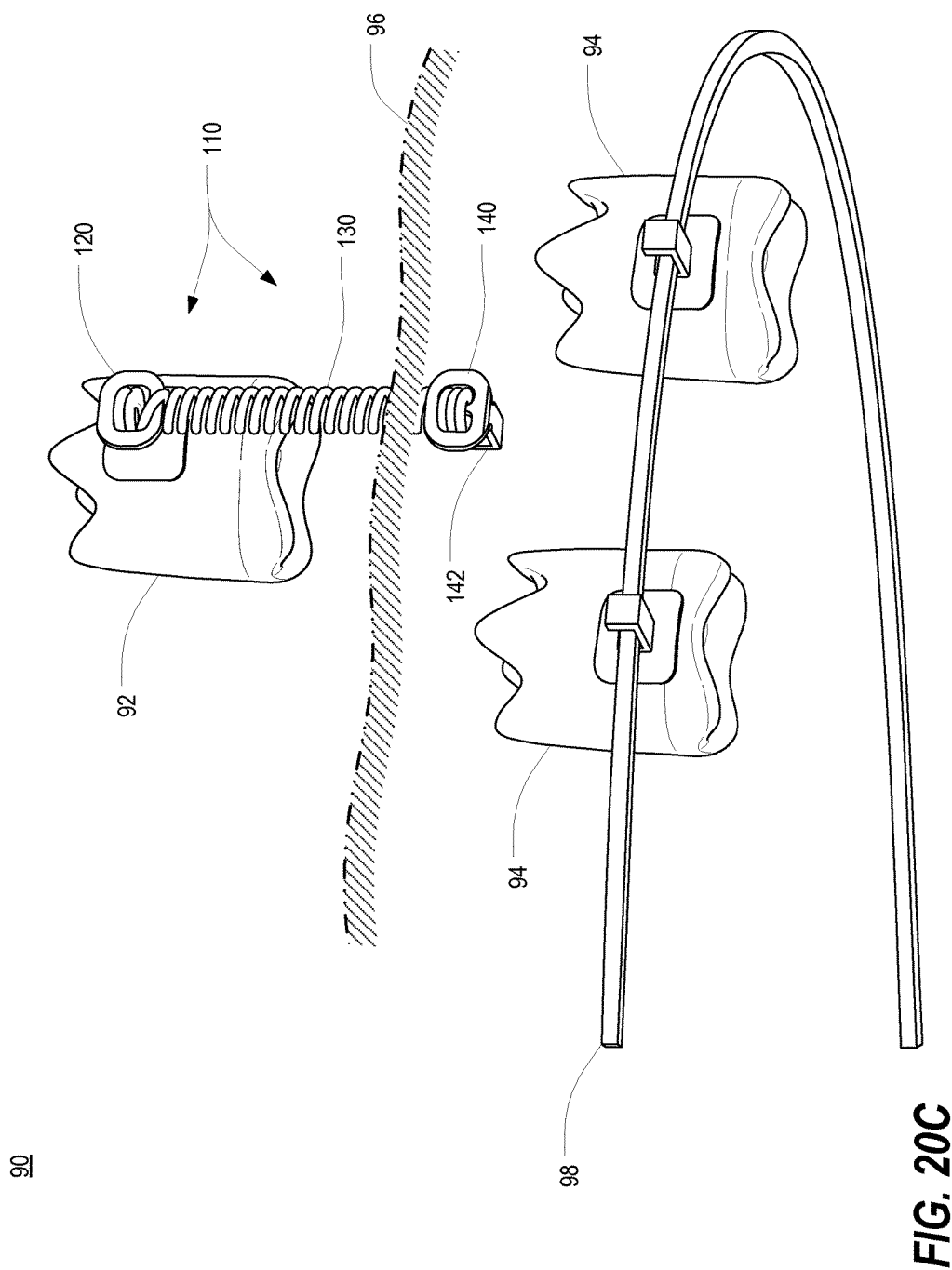

The orthodontic device 110 may be used to quickly adjust the position, location, and/or orientation of an impacted tooth. In this regard, FIGS. 20A-20E are a series of schematic illustrations of the device 110 of FIG. 11 in use in a patient's mouth 90. In FIG. 20A, an impacted tooth 92 is shown as being above the adjacent teeth 94, where it has failed to erupt from the gum tissue 96. It is anticipated that the device 110 may typically be installed during surgery, in which the gum tissue 96 is opened to facilitate access to the impacted tooth 92, but it will be appreciated that in some situations surgery may not be necessary. In FIG. 20B, the bondable bracket 120 is shown installed on the impacted tooth 92, and in FIG. 20C, the spring 130 and anchoring assembly 140 are shown connected to the bondable bracket 120. (It will be appreciated that in some embodiments, the device 110 may be installed as a single unit, while in some embodiments, the bondable bracket 120 may be bonded to the tooth 92 first, and then the spring 130 and anchoring assembly 140 connected afterward.)

Figure 20D:
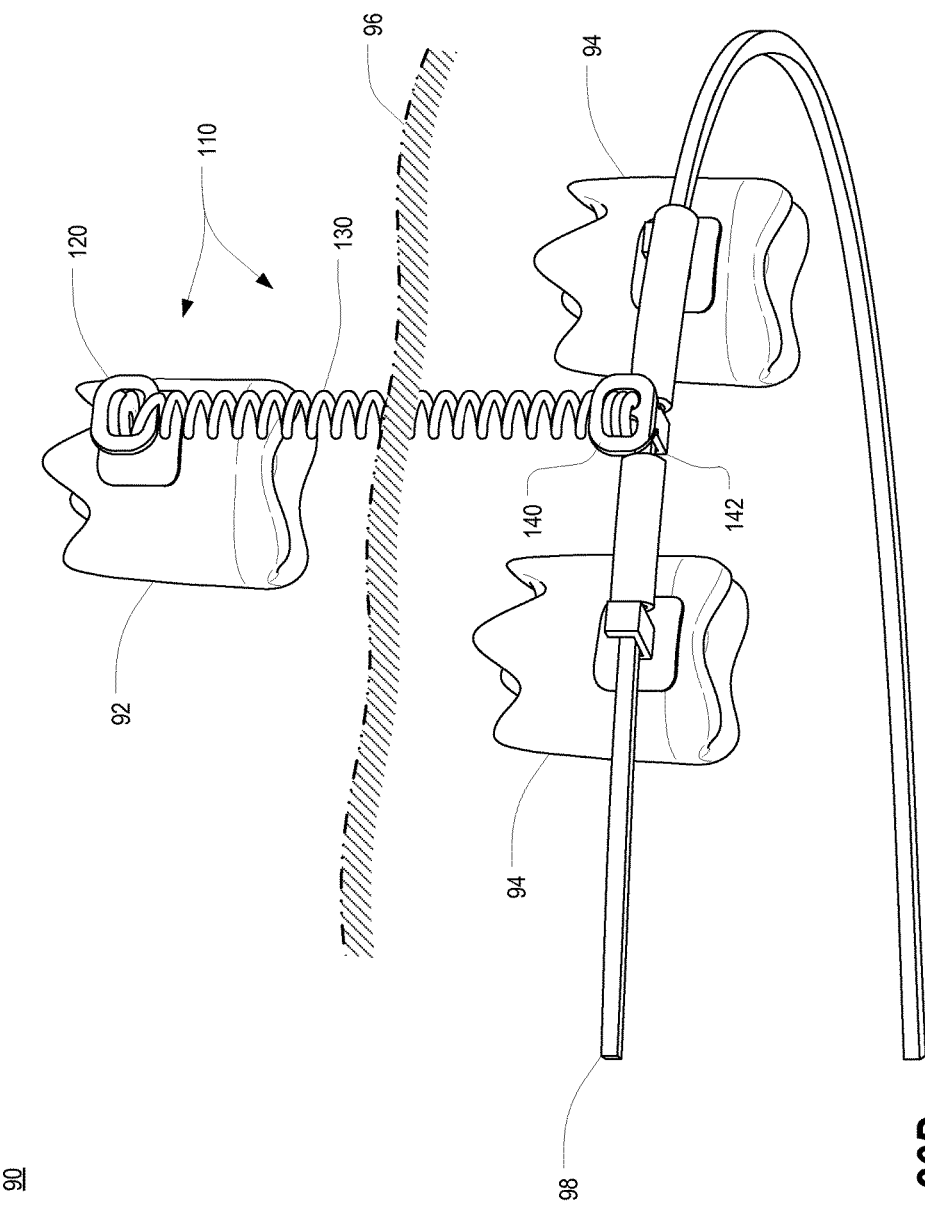
Figure 20E:
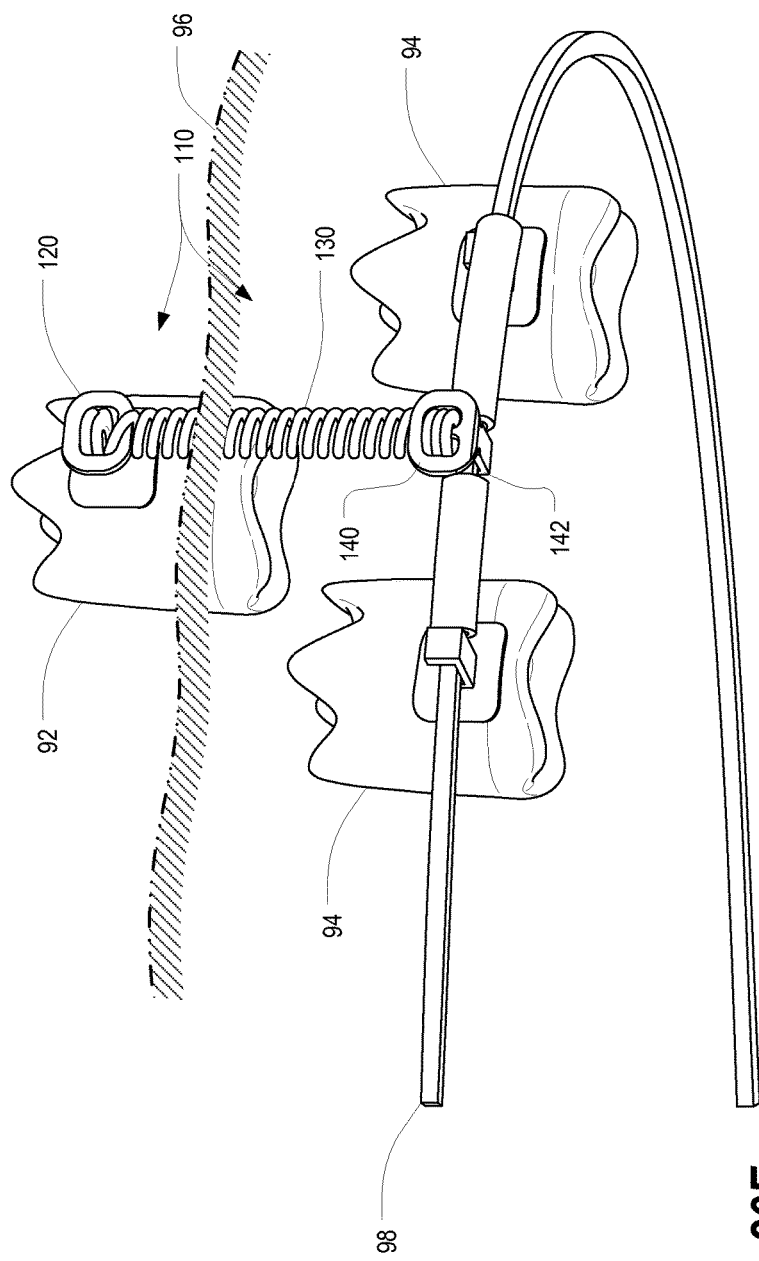

With the bondable bracket 120 bonded to the involved tooth 92, the spring 130 is "activated" or stretched, and the anchoring assembly 140 is attached to the orthodontic archwire 98, as shown in FIG. 20D. With the spring activated, the spring 130 applies a relatively constant and orthodontically-friendly force to the involved tooth 92 over a longer period of time when compared to traditional methods. It is thus potentially possible to carry out surgery on a particular patient a fewer number of times, to make adjustments less frequently, and to reduce the overall amount of time that is required to force eruption of the impacted tooth 92 through the gum tissue 96, as shown in FIG. 10E. Ultimately, the same process may be used to bring the impacted tooth 92 into a proper position between the adjacent teeth 94.

By selecting the shortest possible length of spring 130 that will stretch from the involved tooth 92 to the orthodontic archwire 98 without undergoing permanent deformation, the device 110 will remain active over the longest period of time without the need for adjustment or reactivation by the orthodontist. Ideally, the device 110 would be produced in different "sizes" that differ only in the length of the middle section 136 of the coil spring 130, so that the practitioner could select the appropriate length of device 110 for the particular clinical situation in which it is being used. One contemplated set of sizes includes one size in which the middle spring section 136 is 5 mm in length when in its inactive state, one size in which the middle spring section 136 is 8 mm in length when in its inactive state, and one size in which the middle spring section 136 is 11 mm in length when in its inactive state. If the first and second spring end sections 132,134 are 0.5 mm in length, then the overall length of these three spring sizes would be 6 mm, 9 mm, and 12 mm, respectively.

Figure 21:
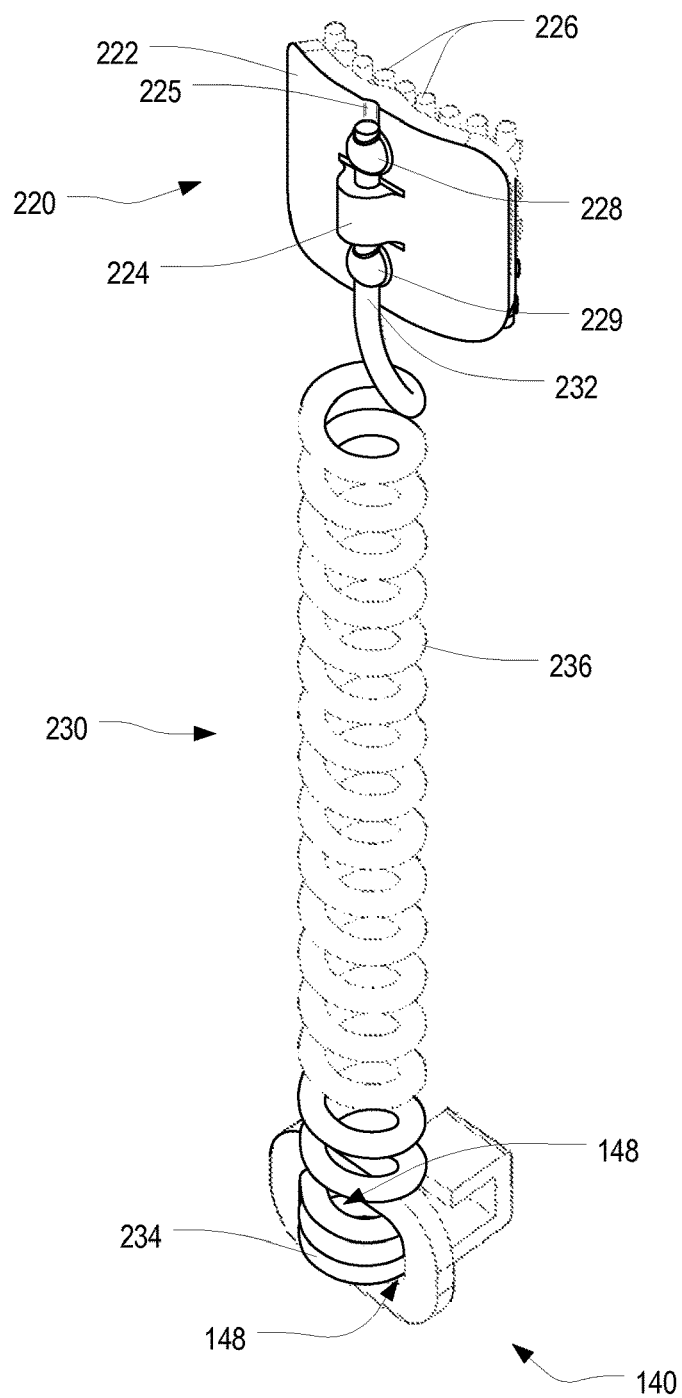
FIG. 21 is a front orthogonal view of an orthodontic device, shown in its activated state, for exposure of impacted teeth in accordance with one or more further preferred embodiments of the present invention.

In various alternative embodiments, a coiled spring may be connected to a bondable bracket in other ways. For example, FIG. 21 is a front orthogonal view of an orthodontic device 210, shown in its activated state, for exposure of impacted teeth in accordance with one or more further preferred embodiments of the present invention. As shown therein, the orthodontic device 210 includes a bondable bracket 220, a spring 230 (shown in its active state) connected at one end to the bracket 220, and an anchoring assembly 140 connected to the other end of the spring 230.

The bracket 220 includes a bondable metal pad or button 222 and a spring attachment portion 224. Like the pads or buttons 22,122 of previously-described embodiments, the pad or button 222 may be bonded to an impacted tooth or other tooth of interest using a conventional dental or orthodontic bonding adhesive. The rear of the pad or button 222 may include a metal retentive mesh 226 where the bonding adhesive (not shown) may be placed. In at least some embodiments, the pad or button 222 is curved so as to better fit the contours of the tooth 92 to which it is to be bonded. Such curvature may be side to side, top to bottom, or both, and different amounts of curvature may be supplied on different bondable brackets 220 so as to facilitate selection of the proper degree of curvature. In this embodiment, the spring attachment portion 224 includes a loop into which a first end 232 of the spring 230 may be inserted.

Figure 22:
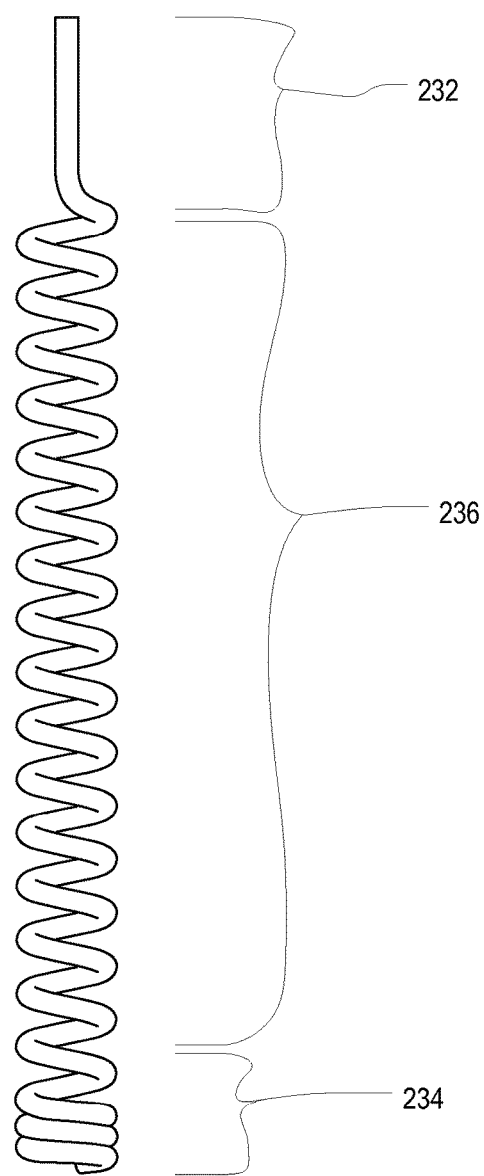
FIG. 22 is a side view of the coiled spring of FIG. 21.

FIG. 22 is a side view of the coiled spring 230 of FIG. 21. The spring 230 includes a first end 232, a second end 234, and a middle section 236. The first end 232 connects to the bondable bracket 220 and the second end 234 connects to the anchoring assembly 140. In the illustrated embodiment, the first spring end 232 is a straight segment that is inserted through the loop 224 of the bondable bracket 220 and multiple coils of the second spring end 234 are wound through conjoined slot openings 148 in the anchoring assembly 140. Other than the straight end 232, the spring 230 may otherwise have characteristics similar to those of the springs 30,130 described previously.

In the illustrated embodiment, the anchoring assembly 140 may be identical to that of FIG. 11, described previously.

Figure 23:
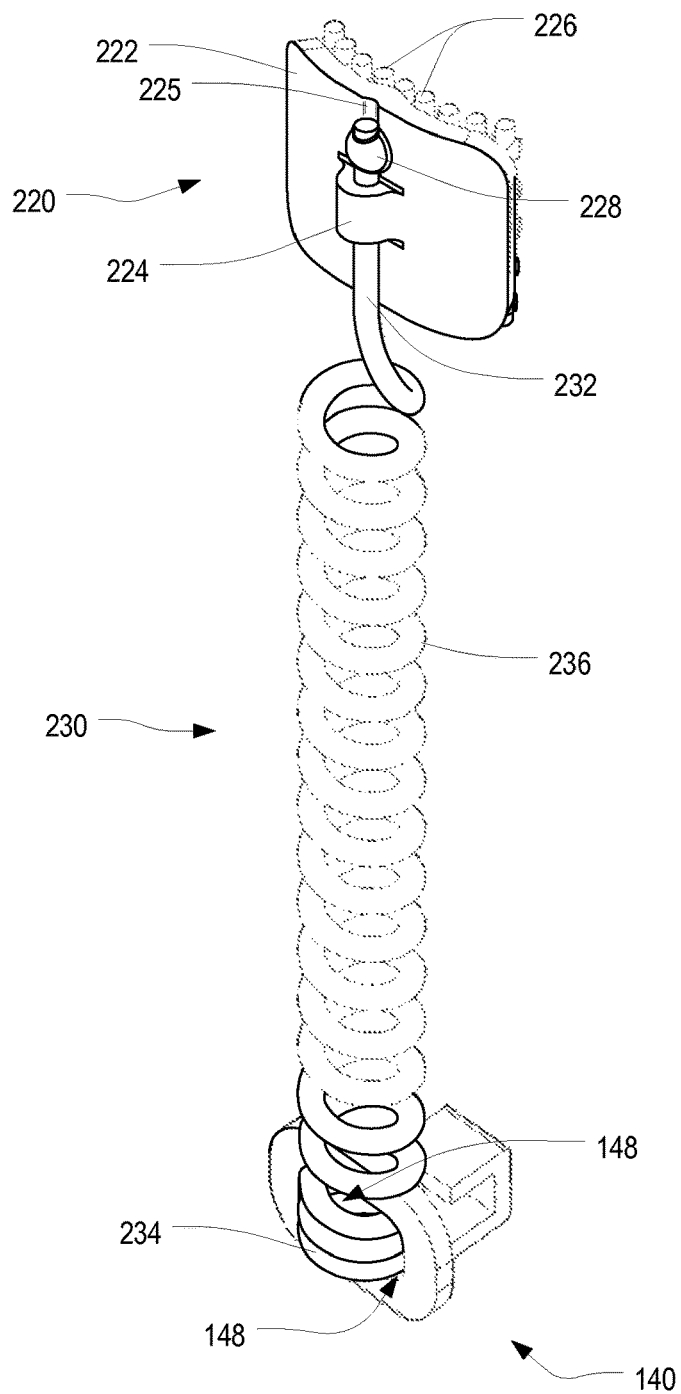
FIG. 23 is a front orthogonal view of the orthodontic device of FIG. 21 but shown with only a single weld.

Referring again to FIG. 21, the straight spring end 232 is connected to the bondable bracket 220 by first inserting the end 232 through the loop 224 and then welding the end 232 to the front of the bracket 220 using at least one weld 228 and, in some cases, a second weld 229. FIG. 21 illustrates the use of two welds 228,229, while FIG. 23 is a front orthogonal view of the orthodontic device 210 of FIG. 21 but shown with only a single weld 228. The welds 228,229 may, in at least some embodiments, be applied via laser welding and/or may, in at least some embodiments, be applied via spot welding. A groove 225 may be provided in the pad or button 222 to increase the surface area, thereby improving the strength and durability of the weld 228. In at least some embodiments, the spring 230 may be heat treated, and in at least some of these embodiments such heat treatment would occur post-welding, thereby providing additional strength and reliability in the welds 228,229.

The orthodontic device 210 may be used to quickly adjust the position, location, and/or orientation of an impacted tooth using methods similar to those described previously, except that in at least some embodiments the first spring end 232 must be permanently attached to the bondable bracket 220 before use. In particularly, after insertion through the loop 224 of the bondable bracket 220, the first spring end 232 is welded to the pad or button 222 such that it cannot thereafter be removed from the loop 224 without destroying at least one of the spring 230, the welds 228,229, or the bracket 220 itself. With the spring 230 connected to the bracket 220, further use of the device 210 may be similar to the usage illustrated, for example, in FIGS. 20C-20E.

Figure 24:
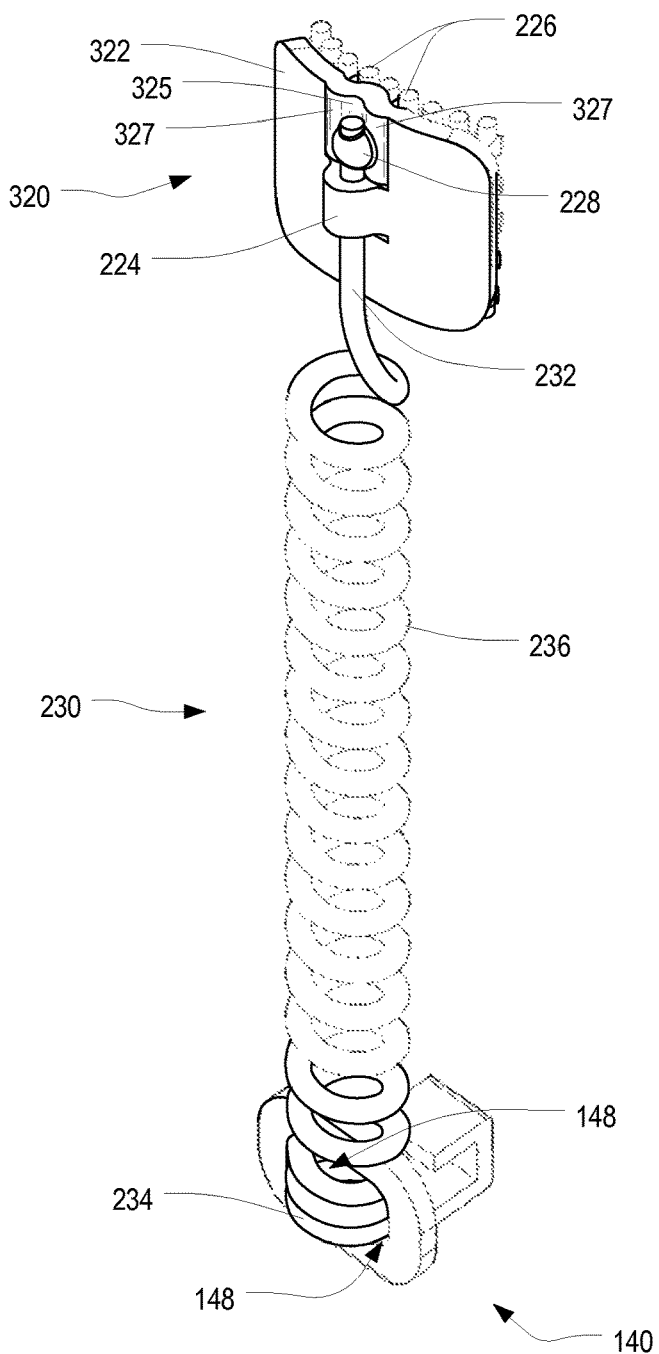
FIG. 24 is a front orthogonal view of an orthodontic device, shown in its activated state, for exposure of impacted teeth in accordance with one or more further preferred embodiments of the present invention.

FIG. 24 is a front orthogonal view of an orthodontic device 310, shown in its activated state, for exposure of impacted teeth in accordance with one or more further preferred embodiments of the present invention. As shown therein, the orthodontic device 310 includes a bondable bracket 320, a spring 230 (shown in its active state) connected at one end to the bracket 320, and an anchoring assembly 140 connected to the other end of the spring 230. The bracket 320 includes a bondable metal pad or button 322 and a spring attachment portion 224. The bracket 320 is somewhat similar to the bracket of FIG. 23 but includes a deeper groove 325 formed between two ridges 327 rising from the face of the pad or button 322. This deeper groove 325 provides further improvement to the strength and durability of the weld 228.

Figure 25:
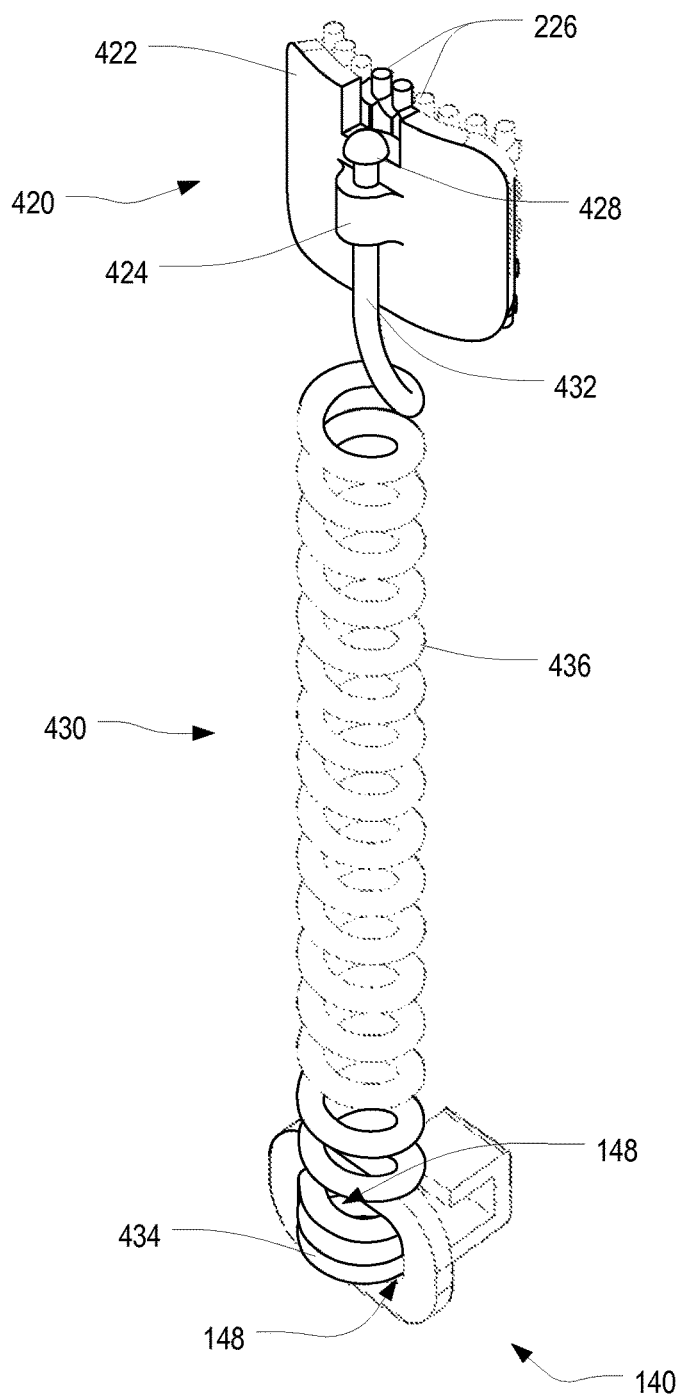
FIG. 25 is a front orthogonal view of an orthodontic device, shown in its activated state, for exposure of impacted teeth in accordance with one or more further preferred embodiments of the present invention.

FIG. 25 is a front orthogonal view of an orthodontic device 410, shown in its activated state, for exposure of impacted teeth in accordance with one or more further preferred embodiments of the present invention. As shown therein, the orthodontic device 410 includes a bondable bracket 420, a spring 430 (shown in its active state) connected at one end to the bracket 420, and an anchoring assembly 140 connected to the other end of the spring 430.

The bracket 420 includes a bondable metal pad or button 422 and a spring attachment portion 424. Like the pads or buttons 22,122,222,322 of previously-described embodiments, the pad or button 422 may be bonded to an impacted tooth or other tooth of interest using a conventional dental or orthodontic bonding adhesive. The rear of the pad or button 422 may include a metal retentive mesh 226 where the bonding adhesive (not shown) may be placed. In at least some embodiments, the pad or button 422 is curved so as to better fit the contours of the tooth 92 to which it is to be bonded. Such curvature may be side to side, top to bottom, or both, and different amounts of curvature may be supplied on different bondable brackets 420 so as to facilitate selection of the proper degree of curvature. In this embodiment, the spring attachment portion 424 includes a loop into which a first end 432 of the spring 430 may be inserted.

Figure 26:
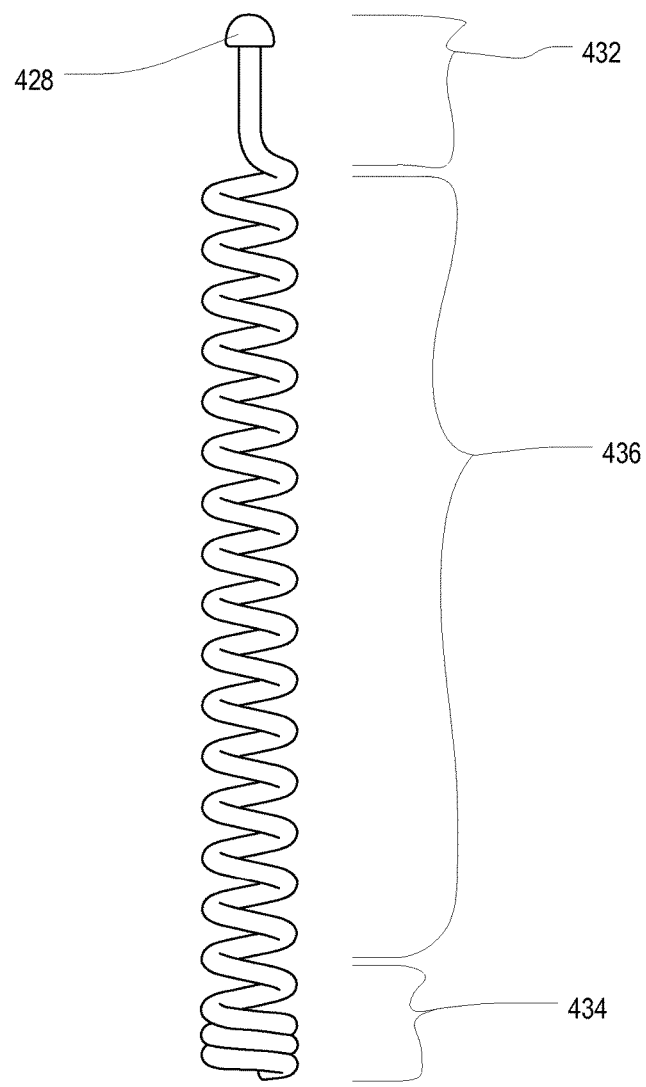
FIG. 26 is a side view of the coiled spring of FIG. 25.

FIG. 26 is a side view of the coiled spring 430 of FIG. 25. The spring 430 includes a first end 432, a second end 434, and a middle section 436. The first end 432 connects to the bondable bracket 420 and the second end 434 connects to the anchoring assembly 140. In at least some embodiments, the spring 430 is initially provided in a state similar to that of the spring 230 in FIG. 22. More particularly, in an initial state, the first spring end 432 is a straight segment that may be inserted through the loop 424 of the bondable bracket 420. After insertion, the first spring end 432 is deformed, such as by melting, to form a "mushroom-" or other shaped head 428. Once the head 428 is formed, the first spring end 432 may no longer be withdrawn from the loop 424. Advantageously, the spring 430 itself may remain free to rotate, at least somewhat, within the loop 424, thereby providing an element of rotational flexibility. Furthermore, because the spring 430 is retained via the head 428, rather than by a weld such as the welds 228,229 of the spring 230 of FIGS. 21-23, there is no risk of a weld breaking. This may be particularly important where such a weld is between two different alloys or other metals, such as between stainless steel and nitinol.

As in FIGS. 21 and 23, multiple coils of the second spring end 434 are wound through conjoined slot openings 148 in the anchoring assembly 140. Other than the straight end 432, the spring 430 may otherwise have characteristics similar to those of the springs 30,130,230 described previously. Also, as in the device 210 of FIGS. 21 and 23, the anchoring assembly 140 may be identical to that of FIG. 11, described previously.

The orthodontic device 410 may be used to quickly adjust the position, location, and/or orientation of an impacted tooth using methods similar to those described previously, except that in at least some embodiments the first spring end 432 must be permanently attached to the bondable bracket 420 before use. In particularly, after insertion through the loop 424 of the bondable bracket 420, the first spring end 432 is deformed, such as by melting the end 432 to form a mushroom head 428, such that it cannot thereafter be removed from the loop 424 without destroying at least one of the spring 430, the mushroom head 428, or the bracket 420 itself. With the spring 430 connected to the bracket 420, further use of the device 410 may be similar to the usage illustrated, for example, in FIGS. 20C-20E.

Figure 27A:
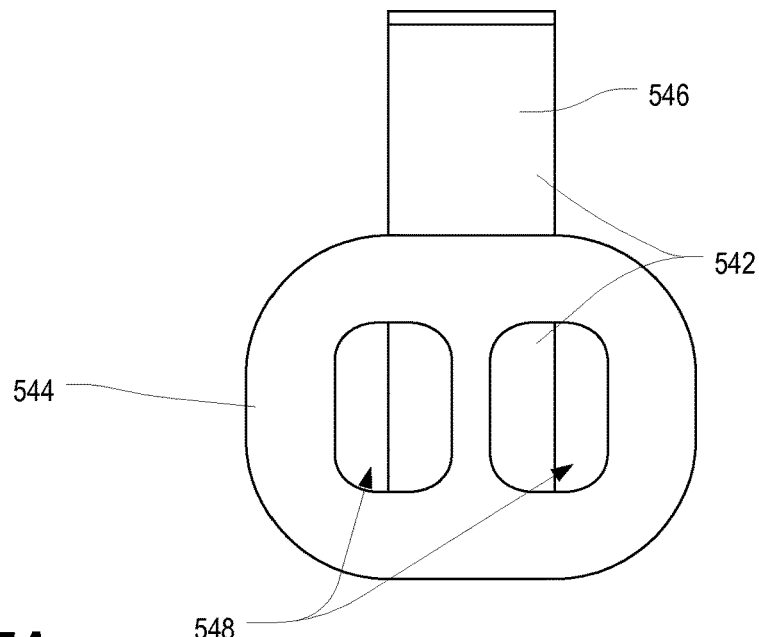
FIGS. 27A and 27B are a front view and a right side view, respectively, of an alternative anchoring assembly.
Figure 27B:
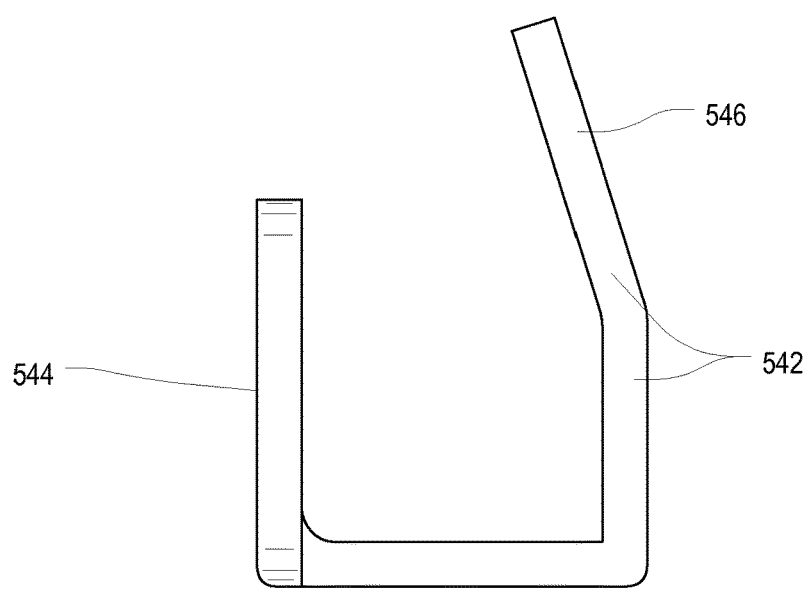

FIGS. 27A and 27B are a front view and a right side view, respectively, of an alternative anchoring assembly 540. Like the anchoring assembly 140 of FIGS. 18 and 19, the anchoring assembly 540 includes an anchoring feature 542 and a spring attachment portion 544. Unlike the anchoring assembly 140 of FIG. 19, the anchoring feature 542 of the alternative anchoring assembly 540 includes an angled tip 546 to facilitate maneuvering the anchoring feature 542, which may be a sort of hook, over an orthodontic archwire 98 or the like. More particularly, the angled tip 546 creates a wider opening in the anchoring feature 542. The hook or other anchoring feature 542 may be anchored to an orthodontic archwire 98 or the like as described elsewhere herein. In at least some embodiments, the angled tip 546 may be crimped into place, after being installed on the archwire 98, to provide an improved, connection. The spring attachment portion 544 may include one or more features for attaching or connecting an end of a spring thereto. For example, in the illustrated embodiment, the spring attachment portion 544 includes a pair of separate slot openings 548 for receiving one or more loops or coils of a coiled spring, but in other embodiments, a pair of conjoined slot openings similar to the conjoined slot openings 148 of FIG. 18 may be provided.

Figure 28:
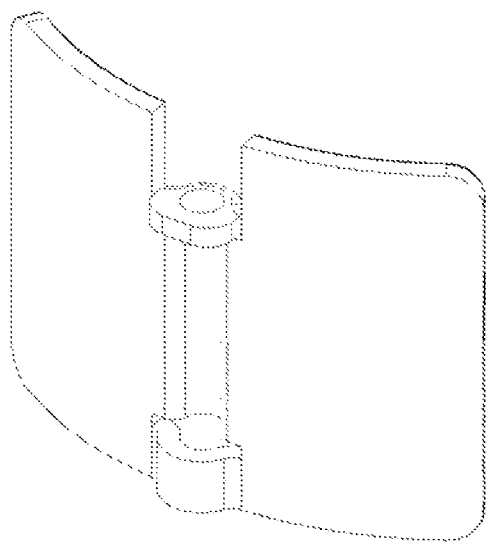
FIG. 28 is a front orthogonal view of an alternative bondable bracket for use in an orthodontic device for exposure of impacted teeth in accordance with one or more further preferred embodiments of the present invention.

FIG. 28 is a front orthogonal view of an alternative bondable bracket 620 for use in an orthodontic device for exposure of impacted teeth in accordance with one or more further preferred embodiments of the present invention. As shown therein, the bondable bracket 620 includes a bondable metal pad or button and a spring attachment portion. Like the pads or buttons 22,122,222,322,422 of previously-described embodiments, the pad or button may be bonded to an impacted tooth or other tooth of interest using a conventional dental or orthodontic bonding adhesive. The rear of the pad or button may include a metal retentive mesh where the bonding adhesive (not shown) may be placed. In at least some embodiments, the pad or button is curved so as to better fit the contours of the tooth 92 to which it is to be bonded. Such curvature may be side to side, top to bottom, or both, and different amounts of curvature may be supplied on different bondable brackets 620 so as to facilitate selection of the proper degree of curvature. In this embodiment, the spring attachment portion includes a first loop into which a first end of a spring may be inserted as well as a second loop or bracket. A groove may extend between the two loops so as to accommodate the spring end.

In at least some contemplated embodiments, an orthodontic device includes a bondable bracket 220 and a spring 230 like those shown in FIG. 23 and an anchoring assembly or archwire bracket 540 like that shown in FIGS. 27A and 27B. In various such embodiments, the bondable metal pad or button 222 is approximately 3.00-4.00 mm wide, 2.00-4.00 mm tall, and 0.20-0.40 mm thick; the loop 224 is approximately 0.50-1.00 mm wide (top to bottom) and 0.20-0.40 mm thick, has an internal radius of approximately 0.10-0.20 mm, and is disposed approximately 0.50-1.00 mm from the top of the pad 222; and the weld 228 is in the form of a welded ball that is approximately 0.40-0.75 mm in diameter. Also in such embodiments, the wire comprising the spring 230 has a diameter of 0.15-0.35 mm, and the coil of the spring 230 has an exterior diameter of approximately 1.50-2.50 mm. Also in such embodiments, the spring attachment portion 544 is approximately 1.50-2.50 mm tall, 2.50-3.50 mm wide, and 0.20-0.40 mm thick; the anchoring feature 542 includes a first portion, which may be a standoff portion, extending perpendicularly from the spring attachment portion, that is approximately 0.75-1.25 mm wide, 2.00-2.50 mm long and 0.20-0.40 mm thick; the anchoring feature 542 includes a second portion, extending perpendicularly from the first portion (and parallel to the spring attachment portion 542), that is 0.75-1.25 mm wide, 1.25-3.00 mm long and 0.20-0.40 mm thick; the angled tip 546 is angled approximately 15-45 degrees from the plane of the second portion of the anchoring feature 542 and is approximately 0.75-1.25 mm wide, 1.50-2.00 mm long and 0.20-0.40 mm thick; the slots 548 are approximately 1.00 mm long and 0.70 mm wide, and separated from one another by 0.20 mm. In one particular embodiment, the bondable metal pad or button 222 is approximately 3.25 mm wide, 2.50 mm tall, and 0.25 mm thick; the loop 224 is approximately 0.65 mm wide (top to bottom) and 0.25 mm thick, has an internal radius of approximately 0.15 mm, and is disposed approximately 0.60 mm from the top of the pad 222; and the weld 228 is in the form of a welded ball that is approximately 0.50-0.60 mm in diameter. Also in at least such particular embodiment, the wire comprising the spring 230 has a diameter of approximately 0.25 mm, and spring coil of the spring 230 has an exterior diameter of approximately 1.60 mm. Also at least in such particular embodiment, the spring attachment portion 544 is approximately 2.0 mm tall, 2.60 mm wide, and 0.25 mm thick; the anchoring feature 542 includes a first portion, which may be a standoff portion, extending perpendicularly from the spring attachment portion, that is approximately 1.00 mm wide, 2.25 mm long and 0.25 mm thick; the anchoring feature 542 includes a second portion, extending perpendicularly from the first portion (and parallel to the spring attachment portion 542), that is 1.00 mm wide, 1.50 mm long and 0.25 mm thick; the angled tip 546 is angled approximately 17.5 degrees from the plane of the second portion of the anchoring feature 542 and is approximately 1.00 mm wide, 1.75 mm long and 0.25 mm thick; the slots 548 are approximately 1.00 mm long and 0.70 mm wide, and separated from one another by 0.20 mm.

In at least some embodiments, the anchoring feature 42, 142,542 is large enough that the interior width or diameter is sufficient to surround not only an archwire 98 but a spacer material, such as a stainless steel sleeve or spring, that surrounds the archwire 98. Also in at least some embodiments, the internal radius (diameter) of the loop 224 is selected to match the diameter or width of the wire of the spring 230.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrange-

What is claimed is:

1. An orthodontic device for effecting vertical movement of an impacted tooth, comprising:
    a bracket including a button or pad that is bondable to an impacted tooth, in a first jaw, the first jaw being an upper jaw or a lower jaw, an archwire adapted to be arranged around the first jaw, and a distinct spring attachment portion;
    an anchoring assembly including an anchoring feature or archwire bracket and a spring attachment portion, wherein the anchoring feature or archwire bracket is coupled directly to the archwire; and
    a spring secured at a first end to the spring attachment portion of the bondable bracket and secured at a second end to the spring attachment portion of the anchoring assembly, wherein the spring extends perpendicularly upward or downward from the archwire and is held in tension between the bondable bracket and the archwire, thereby applying a pulling force to the bondable bracket to pull the bondable bracket vertically toward the archwire.

2. The orthodontic device of claim 1, wherein the bondable bracket is spaced at a distance above or below the archwire such that there is no contact between the bondable bracket and the archwire.

3. The orthodontic device of claim 1, wherein the spring attachment portion of the bondable bracket includes a rigid loop extending from the button or pad.

4. The orthodontic device of claim 3, wherein the first end of the spring extends through the loop.

5. The orthodontic device of claim 1, wherein the spring attachment portion of the bondable bracket is connected to the button or pad via a standoff portion.

6. The orthodontic device of claim 1, wherein the spring attachment portion includes at least one slot through which the spring is routed.

7. The orthodontic device of claim 1, wherein the spring is a coil spring.

8. The orthodontic device of claim 7, wherein the first end of the coil spring is threaded through at least one slot in a spring attachment portion of the bondable bracket.

9. The orthodontic device of claim 7, wherein the coil spring defines a longitudinal axis, and wherein the longitudinal axis of the coil spring is co-planar with a main portion of the button or pad.

10. The orthodontic device of claim 7, wherein the second end of the coil spring is threaded through at least one slot in the spring attachment portion of the anchoring assembly.

11. The orthodontic device of claim 7, wherein the coil spring defines a longitudinal axis, and wherein the longitudinal axis of the coil spring is co-planar with the spring attachment portion of the anchoring assembly.

12. The orthodontic device of claim 7, wherein the coil spring defines a longitudinal axis, and wherein the longitudinal axis of the coil spring is co-planar with a main portion of the anchoring feature or archwire bracket.

13. The orthodontic device of claim 7, wherein the coil spring defines a longitudinal axis, and wherein the longitudinal axis of the coil spring is co-planar with the spring attachment portion of the bondable bracket.

14. The orthodontic device of claim 1, wherein the spring attachment portion is connected to the anchoring feature or archwire bracket via a standoff portion.

15. The orthodontic device of claim 1, wherein the spring attachment portion includes at least one slot through which the spring is routed.

16. The orthodontic device of claim 1, wherein the anchoring feature or archwire bracket includes a hook.

17. The orthodontic device of claim 16, wherein the hook is a round hook.

18. The orthodontic device of claim 16, wherein the hook is a rectangular hook.

19. An orthodontic device for effecting vertical movement of a tooth that has failed to properly push through a gum tissue and is thus an impacted tooth, comprising:
    an anchoring assembly that is attached directly to an archwire adapted to be arranged horizontally around a first jaw, the first jaw being an upper jaw or a lower jaw;
    a bracket including a button or pad that is bondable to a tooth that has failed to properly push through a gum tissue and is thus an impacted tooth, the impacted tooth being in the first jaw, wherein the bracket further includes a distinct spring attachment portion, and wherein the bondable bracket is spaced at a distance above or below the archwire such that there is no contact between the bondable bracket and the archwire; and
    a coiled spring, having a longitudinal axis, secured at a first end to the spring attachment portion of the bracket and secured at a second end to the anchoring assembly such that the longitudinal axis of the coiled spring is oriented perpendicularly to the archwire, wherein the spring applies a pulling force to the bracket such that the bracket is pulled vertically toward the archwire.

* * * * *